United States Patent [19]
Barranger et al.

[11] Patent Number: 5,911,983
[45] Date of Patent: Jun. 15, 1999

[54] GENE THERAPY FOR GAUCHER DISEASE USING RETROVIRAL VECTORS

[75] Inventors: John A. Barranger, Gibsonia; Paul Robbins; Alfred B. Bahnson, both of Pittsburgh, all of Pa.

[73] Assignee: University of Pittsburgh, Pittsburgh, Pa.

[21] Appl. No.: 08/466,597

[22] Filed: Jun. 6, 1995

Related U.S. Application Data

[63] Continuation-in-part of application No. 07/904,809, Jun. 26, 1992, abandoned.

[51] Int. Cl.$^6$ .............................. A61K 48/00; C12N 5/10; C12N 15/86
[52] U.S. Cl. .................. 424/93.21; 424/93.6; 435/320.1; 435/372
[58] Field of Search ................................ 435/69.1, 172.1, 435/172.3, 320.1, 240.2, 366, 372, 372.2, 372.3; 424/93.6, 93.2, 93.21

[56] References Cited

FOREIGN PATENT DOCUMENTS

WO9207943  5/1992  WIPO .

OTHER PUBLICATIONS

"Report and Recommendations of the Panel to Assess the NIH Investment in Gene Therapy", S.H. Orkin and A.G. Arno, Eds, Dec. 1995.
Patrick, A.D., Biochem. J. 97:17C–18C (1965).
Brady, R.O., et al., Biochem. Biophys. Res. Commun. 18:221–225 (1965).
Erickson, A.H., et al., J. Biol. Chem. 260:14319–14324 (1985).
Ho, M.W., et al., Proc. Natl. Acad. Sci. USA 68:2810–2813 (1971).
O'Brien, J.S., et al., Science 241:1098–1101 (1988).
Ginns, E.I., et al., Biochem. Biophys. Res. Commun. 123:574–580 (1984).
Sorge, J., et al., Proc. Nat. Acad. Sci. USA 82:7289–7293 (1985).
Tsuji, S., et al., J. Biol. Chem. 261:50–53 (1986).
Ginns, E.I., et al., Proc. Nat. Acad. Sci. USA 82:7101–7105 (1985).
Tsuji, S., et al., New Engl. J. Med. 316:570–575 (1987).
Tsuji, S., et al., Proc. Natl. Acad. Sci. USA 85:2349–2352 (1988).
Firon, N., et al., Am. J. Hum. Genet. 46:527–532 (1990).
Rappeport, J.M., et al., Birth Defects: Original Article Series 22,1:101–109 (1986).
Barranger, J.A., et al., Japanese J. of Inher. Met. Disease 51:45–71 (1989).
Takasaki, S., et al., J. Biol. Chem. 259:10112–10117 (1984).
Furbish, F.S., et al., Biochem. Biophys. Acta. 673:425–434 (1981).
Miller, A.D., Blood 76:271–278 (1990).
Miller, D.G., et al., Mol. Coll. Biol. 10:4239–4242 (1990).
Bodine, D.M., et al., Exp. Hematol. 19:206–212 (1991).
Nolta, J.A., et al., Blood 75:787–797 (1990).
Correll, P.H., et al., Proc. Natl. Acad. Sci. USA 86:8912–8916 (1989).
Scherdin, U., et al., J. Virol. 64:907–912 (1990).
McLaughlin, S.K., et al., J. Virol. 65:1963–1973 (1988).
Hunter, L.A., et al., J. Virol. 66:317–324 (1992).
Tratschin, J.D., et al., Mol. Cell. Biol. 5:3251–3260 (1985).
Hermanat, P.L., et al., Proc. Natl. Acad. Sci. USA 81:6466–6470 (1984).
Lebkowski, J.S., et al., Mol. Cell. Biol. 8:3988–3996 (1988).
Samulski, R.J., et al., EMBO J. 10:3941–3950 (1991).
Kotkin, R.M., et al., Proc. Natl. Acad. Sci. USA 87:2211–2215 (1990).
Pear, W.S., et al., Proc. Natl. Acad. Sci. USA 90:8392–8396, 1993).
Shpall, E.J., et al., Journal of Hematotherapy 3:145–147 (1994).
Miller, A.D., et al., Human Gene Therapy 1:5–14, (1990).
Bahnson, A.B., et al., Gene Therapy 1(3):176–184, (1994).
Armentano et al., J. Virol. 61:1647–1650, (1987).
Hock et al., Blood 74:876–881, (1989).
Berenson, R. J., et al., Blood 77(8):1717–1722, (1991).
Bregni, M., et al., Blood 80:1418–1422, (1992).
Nimgaonkar, M.T., et al., Gene Therapy 1:201–207, (1994).
Barranger, J.A. et al., Intl. Pediatrics 10:5–9, (1995).
Sanger, F., et al., Proc. Natl. Acad. Sci. USA 74:5463–5467 (1977).
Chen, C., et al., Mol. Cell Biol. 7:2745–2752 (1987).
Ohashi, T., et al., J. Biol Chem. 266:3661–3667 (1991).
Barnevald, R.A., et al., Eur. J. Biochem. 134:585–589 (1983).
Eppig, J.J., et al., Nature 269:517–518 (1977).
Barranger, J.A., N. Eng. J. Med. 311:1629–1631 (1984).
Gregory, S.H., et al., J. Leukocyte Biol. 43:67–79 (1988).
Stanley, E.R., et al., J. Biol. Chem. 252:4305–4312 (1977).
Langley, K.E., et al., Arch. Biochem. Biophys. 295(1):21–28, 1992).
Danos, O., et al., Proc. Natl. Acad. Sci. USA 85:6460–6464, 1988).

Primary Examiner—David Guzo
Attorney, Agent, or Firm—Baker & Botts, LLP

[57] ABSTRACT

The present invention relates to gene therapy for Gaucher disease using retroviral vectors which express the glucocerebrosidase gene. Methods are provided for transduction of autologous hematopoietic stem cells (e.g., human CD34+ cells) with these vectors and for transplantation of the transduced cells into a Gaucher disease patient to provide therapeutically effective levels of glucocerebrosidase activity. The invention also provides for retroviral vectors that express the glucocerebrosidase gene, and for human hematopoietic cells that contain the retroviral vector.

22 Claims, 38 Drawing Sheets

LANE 1:GC #1
LANE 2:GC #4
LANE 3:GC #5
LANE 4:GC #25
LANE 5:GC #31
LANE 6:NIH 3T3
LANE 7:0637D

LANE 1:MFG-GC(2pg)
LANE 2:MFG-GC(5pg)
LANE 3:MFG-GC(10pg)
LANE 4:GC #31
LANE 5:GC #25
LANE 6:GC #5
LANE 7:GC #4
LANE 8:GC #1

|  | SOUTHERN | WESTERN | ENZYMATIC ACTIVITY |
|---|---|---|---|
|  | COPIES/CELL | CRIM INTENSITY | AMOUNT X BACKGROUND |
| 3T3 CELLS | | | |
| N2-SV-GC | 1 | 1 | 1-2 |
| MFG-GC | 1 | 1 | 5-10 |
| LTBMC | | | |
| N2-SV-GC | ND | ND | ND |
| MFG-GC | 1-2 | 10 | 10 |
| CFU-S$_{12}$ | | | |
| N2-SV-GC | 1-2 | 1 | 1-2 |
| MFG-GC | 1-2 | 10 | 5-10 |

ND=NOT DONE

FIG.6

|  | N2-SV-GC (n=2) | | | | MFG-GC (n=9) | | | |
|---|---|---|---|---|---|---|---|---|
|  | SOUTHERN | WESTERN | ENZYMATIC ACTIVITY | | SOUTHERN | WESTERN | ENZYMATIC ACTIVITY | |
|  | COPIES/CELL | CRIM INTENSITY | AMOUNT X BACKGROUND | | COPIES/CELL | CRIM INTENSITY | AMOUNT X BACKGROUND | |
| BONE MARROW | 1-2 | 1 | NS | | 1-2 | 10 | 4-10 | |
| SPLEEN | 1-2 | 1 | 0 | | 1-2 | 10 | 3-5 | |
| LIVER | 0.1-0.2 | 0 | 0 | | 0.1-0.2 | 1-2 | 2-6 | |
| LUNG | 0.1-0.2 | 0 | 0 | | 0.3 | 1-2 | 2-3 | |
| THYMUS | 1-2 | NS | NS | | 1-2 | 0-2 | 1-3 | |
| LEUKOCYTES | PCR+ | NS | NS | | PCR+ | NS | NS | |
| LYMPH NODE | ND | ND | ND | | 0.5 | 2 | 5-15 | |

NS=INSUFFICIENT MATERIAL    ND=NOT DONE

FIG.11

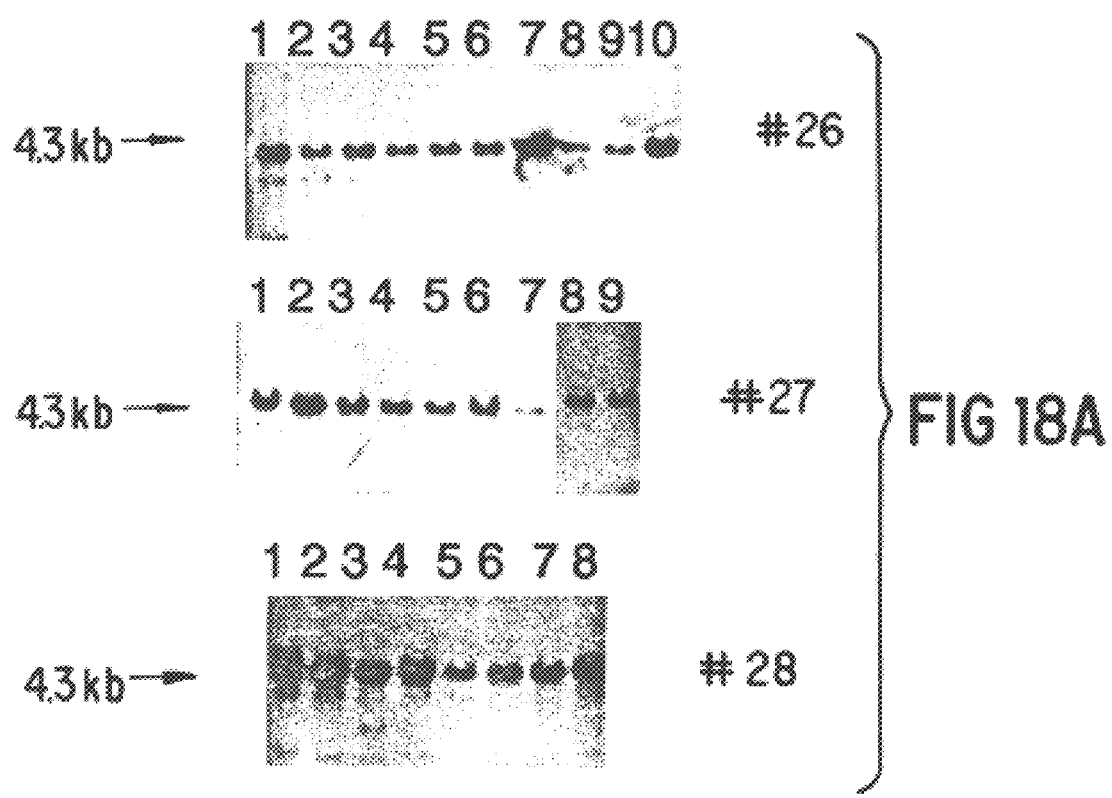

GENE THERAPY FOR GAUCHER DISEASE USING RETROVIRAL VECTORS

SPECIFICATION

This application is a continuation-in-part of our application Ser. No. 07/904,809, filed Jun. 26, 1992, now abandoned. This invention was made with funding from the U.S. Government, which has certain rights therein.

BACKGROUND OF THE INVENTION

Gaucher disease is the name given to a group of lysosomal storage disorders caused by mutations in the gene that codes for an enzyme called glucocerebrosidase ("GC"). Gaucher disease is caused by deficiency of GC as reported by Patrick, A. D., *Biochem. J.* 97:17C (1965) and Brady, R. O., et al., *Biochem. Biophys. Res. Commun.* 18:221 (1965). All of the mutations in the gene alter the structure and function of the enzyme which lead to an accumulation of the undegraded glycolipid substrate glucosylceramide, also called glucocerebroside, in cells of the reticuloendothelial system. Each particular mutation of the human GC gene leads to a clinical disease collectively known as Gaucher disease. These disorders are usually classified into three types; type 1 (non-neuronopathic), type 2 (acute neuronopathic) and type 3 (subacute neuronopathic), the type depending on the presence and severity of neurologic involvement. Gaucher disease is the most prevalent Jewish genetic disease and the most common lysosomal storage disease.

GC is a monomeric, membrane-associated, hydrophobic glycoprotein with a molecular weight of 65,000 daltons. Human GC contains 497 amino acids and is translated as a precursor protein with a 19 amino acid hydrophobic signal peptide which directs its co-translational insertion into the lumen of the endoplasmic reticulum-golgi-lysosome complex as reported by Erickson, A. H., et al., *J. Biol. Chem.* 260: 14319 (1985). GC acts at the acidic pH of the lysosome to hydrolyze beta-glucosidic linkages in complex lipids ubiquitously found in all membranes to form the byproducts of glucose and ceramide. The catalytic activity of GC is increased in vitro by detergents, lipids, and in vivo by a naturally occurring activator known as sphingolipid activator protein-2 (SAP-2 or saposin C). See, Ho, M. W., et al., *Proc. Natl. Acad. Sci. USA* 68:2810 (1971); and O'Brian, J. S., et al., *Science* 241:1098 (1988).

Human GC cDNA was first cloned as described by Ginns, E. I., et al., *Biochem. Biophys. Res. Commun.* 123:574 (1984). Subsequent characterizations of other GC cDNA clones by, for example, Sorge, J., et al., Proc. Nat. Acad. Sci. USA 82:7289 (1985) and Tsuji, S., et al., *J. Biol. Chem.* 261:50 (1986), have led to the elucidation of the complete nucleotide sequence of human GC. As reported by Ginns, E. I., et al., *Proc. Nat. Acad. Sci. USA* 82:7101 (1985), the GC gene was localized to human chromosome 1q21 by in situ hybridization. Tsuji, S., et al., *New Enql. J. Med.* 316:570 (1987), have shown that the GC gene comprises 11 exons and 10 introns spanning approximately 7 Kb.

While more than twenty mutations in the human GC gene are known, only two are common. See, Tsuji, S., et al., *Proc. Natl. Acad. Sci. USA* 85:2349 (1988). The two common mutations account for approximately 70% of the mutant alleles, as reported by Firon, N., et al., *Am. J. Hum. Genet.* 46:527 (1990). Mutant GC genes code for aberrant proteins that are either catalytically altered or unstable and rapidly disappear from the cell.

Although GC is deficient in all of a subject's cells, for unknown reasons, the accumulation of the substrate glucosylceramide occurs virtually only in macrophages. Gaucher disease is unique among lysosomal storage disorders for this reason, that is, causing storage within only one cell type. This characteristic of the pathobiology of the disease has led to the development of two successful treatment strategies based on correcting the enzyme deficiency in macrophages.

The first of the two Gaucher disease treatments based on this strategy is allogeneic bone marrow transplantation, which results in the repopulation of affected tissues with enzyme-competent macrophages. See, Rappeport, J. M., et al., *Birth Defects: Original Article Series* 22,1:101 (1986). The second approach to treatment which has resulted in clinical improvement in Gaucher disease patients is macrophage-targeted enzyme replacement. This treatment takes advantage of naturally occurring mannose receptors on macrophages and the exposition of accessible mannose receptors in the oligosaccharides of glucocerebrosidase to efficiently deliver the enzyme to macrophages. See, Barranger, J. A., et al., *Japanese J. of Inher. Met. Disease* 51:45 (1989); Takasaki, S., et al., *J. Biol. Chem.* 259:10112 (1984); and Furbish, F. S., et al., *Biochem. Biophys. Acta.* 673:425 (1981). While both of these approaches to treating Gaucher disease are important because they provide some means of therapy where none previously existed, both approaches have significant limitations. Allogeneic bone marrow transplantation has associated with it morbidity and mortality risks that are unacceptable for many patients. Further, HLA matched bone marrow donors do not exist for the majority of patients. As for macrophage-targeted enzyme replacement, it is currently an expensive and life-long therapy; thus, it should be reserved for only the most severely ill patients.

Despite the limitations of these two therapies, their successes have demonstrated that enzymatic correction of only one cell type, the macrophage, results in effective therapy for Gaucher disease. From the point of view of developing somatic cell gene therapy for Gaucher disease, the fact that marrow transplantation is effective demonstrates that bone marrow stem cells are an appropriate target cell to which to transfer a "therapeutic" gene. Further, because of the pivotal role of macrophages in Gaucher disease, alternative target cells to be considered for gene transfer are the committed macrophage precursors, peripheral blood monocytes, or cultures of bone marrow which are capable of producing macrophage precursors.

To be an effective permanent treatment for any disease capable of being treated by gene therapy, the transfer and sustained expression of genes in cells important to the pathogenesis of the particular disease is required. Sufficient expression of a transduced GC gene in the progeny of pluripotent bone marrow stem cells would likely correct the deficiency of the enzyme in all cell series including monocytes/macrophages. Experience from allogeneic marrow transplantation and macrophage-targeted enzyme replacement supports the idea that gene therapy would provide a cure provided adequate expression of the GC gene were achieved in a sufficient number of macrophages.

Much experience has been gained recently to evaluate the efficiency of gene transfer and expression in bone marrow stem cells using replication defective retroviral vectors. See, e.g., Miller, A. D., *Blood* 76:2 (1990) and Miller, D. G., et al., *Mol. Coll. Biol.* 10:4239 (1990). Most of the studies of retroviral vectors have been conducted in the mouse model of bone marrow transplantation. Recent data show that 10–20% of stem cells can be transduced and survive to repopulate marrow. See, Bodine, D. M., et al., *Exp. Hematol.* 19:206 (1991). Many fewer studies have been conducted in larger animals and, at the present time, experimental conditions have not yet been fully optimized. For the mouse model, critical parameters for efficient retroviral gene transfer and repopulation of bone marrow include high titer virus producer cell lines (VPL), pretreatment of mice with 5-fluorouracil (5-FU) to initiate stem cell cycling, preculture of bone marrow with growth factors including IL-3 and IL-6 and stem cell factor (SCF). Several studies have shown that the GC gene can be transferred to murine bone marrow stem cells and their progeny, but until recently none had demonstrated expression of enzymatic activity in macrophages in vivo. See, Nolta, J. A., et al., *Blood* 75:75 (1990) and Correll, P. H., et al., *Proc. Natl. Acad. Sci. USA* 86:8912 (1989).

Retroviral vectors for use in gene therapy require dividing cells in order to integrate and they have a small, but finite chance of interrupting an essential gene or altering expression of a gene proximate to the site of integration of the retroviral provirus. However, the proviral integration may be preferentially directed to transcriptionally active regions of the genome as described by Scherdin, U., et al., *J. Virol.* 64; 2:907 (1990). These requirements of retroviral vectors are believed to contribute to the small number of stem cells that can be transduced, since only a portion of the stem cell population is cycling even under optimal experimental conditions. See, McLaughlin, S. K., et al., *J. Virol.* 65:1963 (1991).

For these and other reasons, the small helper-dependent human DNA parvovirus known as adeno-associated virus ("AAV") has recently received attention as a vector that could be useful for gene therapy. See, Hunter, L. A., et al., *J. Virol.* 66:317 (1992); Tratschin, J. D., et al., *Mol. Cell. Biol.* 5:3251 (1985); Hermanat, P. L., et al., *Proc. Natl. Acad. Sci. USA* 81:6466 (1984); and Lebkaski, J. S., et al., *Mol. Cell. Biol.* 8:3988 (1988). A lytic growth cycle for wild AAV requires infection with a helper virus, e.g., adenovirus type 5. In the absence of helper virus, AAV integrates into the host genome by hybridization between the AAV terminal repeats (TR) and host sequences in a stable manner thereby establishing a permanent latent infection. In human cells, this integration occurs preferentially in a single silent site in human chromosome 19. See, Samulski, R. J., et al., *EMBO J.* 10:3941 (1991); Kotkin, R. M., et al., *Proc. Natl. Acad. Sci. USA* 87:2211 (1990).

In order to develop gene therapy that would be useful for the treatment of Gaucher disease as well as other hematopoietic disorders, new vectors are needed that allow efficient gene transfer to stem cells and at the same time direct expression of the transferred gene. Thus far there has not been a vector that can transduce and sustain the expression of the human GC gene in bone marrow stem cells and their progeny. Accordingly there is a need for such a vector which could be used in gene therapy for Gaucher disease.

SUMMARY OF THE INVENTION

Accordingly, it is a primary object of the present invention to provide replication defective retroviral vectors that are able to transduce and sustain the expression of the human GC gene in mammalian bone marrow stem cells and their progeny.

Another object of the present invention is to provide replication defective retroviral vectors capable of transducing and expressing GC activity in committed macrophage precursors.

Still another object of the present invention is to provide replication defective retroviral vectors capable of transducing and expressing GC activity in macrophages.

These and other objects of the present invention are achieved by one or more of the following embodiments.

In another aspect, the invention features the replication defective retroviral vectors MFG-GC and R-GC.

In still another aspect the invention features mammalian bone marrow stem cells transduced with MFG-GC or R-GC.

In yet another aspect the invention features mammalian macrophage precursors transduced with MFG-GC or R-GC.

In preferred embodiments, the invention features a method of treating Gaucher disease in a patient with Gaucher disease, comprising administering to said patient a therapeutically effective amount of mammalian bone marrow cells or mammalian macrophages transduced with MFG-GC or R-GC, such that the transduced cells are stably maintained in the patient and express therapeutic levels of glucocerebrosidase.

In other preferred embodiments, the invention features a method of treating Gaucher disease in a human patient, comprising administering a therapeutically effective amount of human bone marrow cells or human macrophages transduced with MFG-GC or R-GC, such that the transduced cells are stably maintained in the patient and express therapeutic levels of glucocerebrosidase.

In another aspect, the invention features replication defective retroviral vectors containing the GC gene and capable of transducing and long term expression of the GC gene in ex vivo or in vivo gene therapy treatment.

Other features and advantages of the invention will be apparent from the following description of the preferred embodiment, and from the claims.

BRIEF DESCRIPTION OF THE DRAWINGS

The invention may be better understood by reference to the following figures.

FIG. 6 Chart showing results of Southern nd Western analyses, and enzymatic activity of cells infected by the MFG-GC and N2-SV-GC vectors. Results of assays on 3T3 cells, spleen colonies at day 12 (CFU-S$_{12}$) and long term bone marrow cultures (LTBMC) are shown.

FIG. 11 Table comparing MFG-GC and N2-SV-GC retroviral vectors by Southern and Western blots, enzymatic activity in 3T3 cells, spleen colonies, LTBMC, and tissues of mice surviving longer than four months after reconstitution with bone marrow infected by co-cultivation with each of the two viral producer lines.

FIG. 18A Photograph of Southern blots of DNA from 27 individual secondary CFU-$S_{12}$ spleen colonies from three mice that received bone marrow transplants from primary long term reconstituted mice and probed with full length human GC cDNA. Lanes 1–10 contain DNA from spleen colonies isolated from mouse #26; lanes 11–19 contain DNA from spleen colonies isolated from mouse #27; lanes 20–27 contain DNA from spleen colonies isolated from mouse #28; lane 28 contains genomic DNA isolated form an age-related control; and lanes 29–31 contain standards for estimating copy number (0.2, 0.5, and 1.0 copies/cell, respectively).

DETAILED DESCRIPTION OF THE INVENTION

Figure 1:
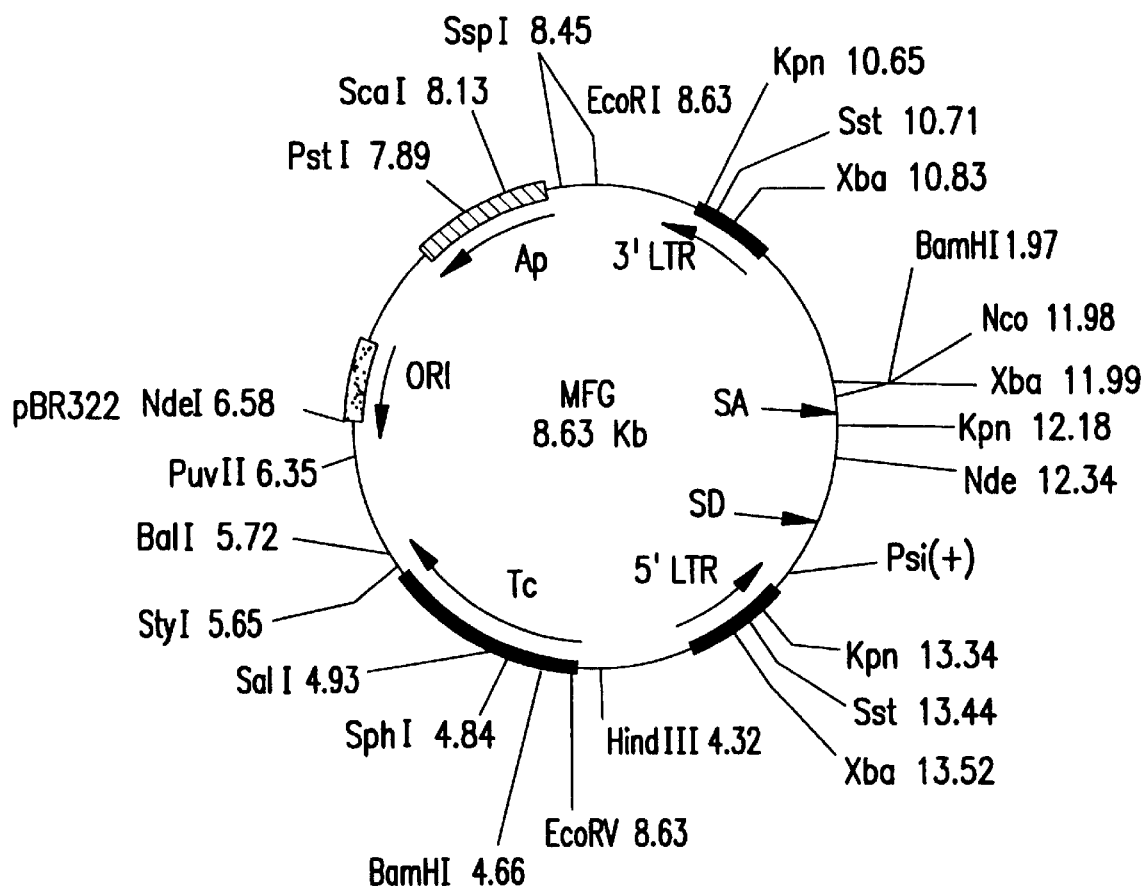
FIG. 1 Restriction site map of the MFG vector.

Gene therapy for Gaucher disease may be accomplished using a viral vector to introduce the GC gene into hematopoietic cells to genetically correct the inability to synthesize functional GC enzymatic activity. In a particular embodiment, a retroviral vector may be used. Vectors which may be used include, but are not limited to, N2 (Armentano et al., J. Virol. 61:1647–1650), 1987), LNL6 (Hock et al., Blood 74:876–881, 1989) and MFG (published PCT application WO92/07943, published May 14, 1992).

The retroviral vector is engineered to contain the human GC gene, using standard recombinant DNA techniques known to those skilled in the art (*Current Protocols in Molecular Biology*. Ausubel, F. et al., eds., Wiley and Sons, New York 1995). The human GC gene can be cloned into an MFG vector to create MFG-GC, in one embodiment, or to create the R-GC vector, in another embodiment. The embodiment, R-GC, is a vector that is derived from MFG-GC, but which has an additional safety feature—an insertion of a SacII linker into the gag sequence to cause a frameshift that prevents the synthesis of gag-related peptides. In other embodiments, safer retroviral vectors may be produced by altering the gag coding sequence with the insertion of stop codons or by mutation of the start codon in the sequence, so that gag-related peptides are not synthesized.

The vectors of the invention may be used in ex vivo or in vivo gene therapy.

Stocks of the retroviral vector may be produced from packaging cell lines that provide the necessary structural proteins (Miller, A. D., Human Gene Therapy 1:5–14, 1990) and enable a replication—defective vector stock to be produced.

Quantitation of the vector stock is performed by using standard assays, including plaque formation on suitable target cells, virus protein assays (e.g., p.24), or measurement of the activity of a transduced gene (i.e., GC activity). High titer producer clones may be chosen for use as a source material.

Gene Transfer and Expression in CD34+ Cells From Blood

CD34+ cells contain a percentage of pluripotent stem cells capable of reconstituting the bone marrow in primates and man (Berenson, R. J., et al., *Blood* 77(8):1717–1722, 1991; Shpall, E., et al., *Blood* 82:321, 1993). Studies have shown that the human peripheral blood CD34+ cell (PBSC) can be transduced by retroviral vectors (Bregni, M., et al., *Blood* 80:1418–1422, 1992). Because of the ability to concentrate CD34+ cells in a small volume, the logistics of ex vivo transduction become greatly simplified. Furthermore, the ratio of virus to stem cell in infection protocols can be enhanced, leading to more efficient transduction. Because of this economy and because the bone marrow of patients with Gaucher disease are frequently "packed" (full of cellular material and scar; they frequently can not be aspirated), the PBSC are particularly ideal cells for gene transfer/therapy studies.

For gene therapy treatment, granulocyte colony stimulating factor (G-CSF) may be administered to an individual in order to increase the number of CD34+ cells circulating in the blood. In an ex vivo protocol, leukopheresis may be used to collect the white blood cells. Density gradient separation of peripheral blood mononuclear cells (MNC) may be performed. CD34+ cells may be enriched from the MNC by immunoaffinity purification. This enrichment generates a stem cell population that optimizes the permanence of gene transfer due to its pluripotent capability.

The enriched CD34+ cell population may be transduced with the supernatant from an amphotropic producer cell line that generates a high titer retroviral vector stock. In a preferred aspect of the invention, R-GC is the retroviral vector that is used to transduce the CD34+ cells, for gene therapy of Gaucher patients.

The transduced CD34+ cells may be assayed for transduction efficiency by techniques known to those skilled in the art, including PCR identification of the GC gene, Southern blot determination of gene copy number, GC enzymatic assay, and immunocytochemistry to detect the GC protein (Bahnson, A. B., et al., Gene Therapy 1:176–184, 1994; Nimgaonkar, M. T., et al., Gene Therapy 1:1–7, 1994; Barranger, J. A. et al., *Intl. Pediatrics* 10:5–9, 1995).

Upon the establishment of an autologous R-GC-transduced CD34+ cell population, the cells are transfused back into a Gaucher patient. Clinical progress is monitored by ongoing analysis of peripheral blood leukocytes (PBL) to determine the presence of the GC gene (PCR, Southern blotting) and the activity of the GC enzyme. Other clinical parameters that may be used to assess patient status include routine blood profiling including hemoglobin level and platelet count, size of liver and spleen, biopsy of bone marrow and x-rays of long bones and the pelvis (see FIG. 40).

EXAMPLE 1
Construction of MFG-GC Vector

The starting vector (MFG) from which a replication defective retroviral vector containing the human GC gene (MFG-GC) was constructed as described in published PCT application WO92/07943, published May 14, 1992. (ATCC accession number ATCC 68,754) The physical structure of the MFG vector is shown in FIG. 1. The features of the present MFG-GC vector deposited at the American Type Culture Collection, 12301 Parklawn Drive, Rockville, Md. 20852 on Apr. 8, 1994 and given the (ATCC accession number 75733) are that the GC cDNA is transcribed by the retrovirus long terminal repeats ("LTR") and the position of the start codon of the GC cDNA is placed exactly at the start codon of the deleted envelope protein gene. No internal promoter or dominant selectable marker is included in the construct. Additionally, there is a Sac II polylinker at the ATG of gag which may further reduce the possibility of the replication defective vector recombining to produce replication competent virus. GC cDNA is inserted into an Nco I/Bam HI site.

Figure 2:
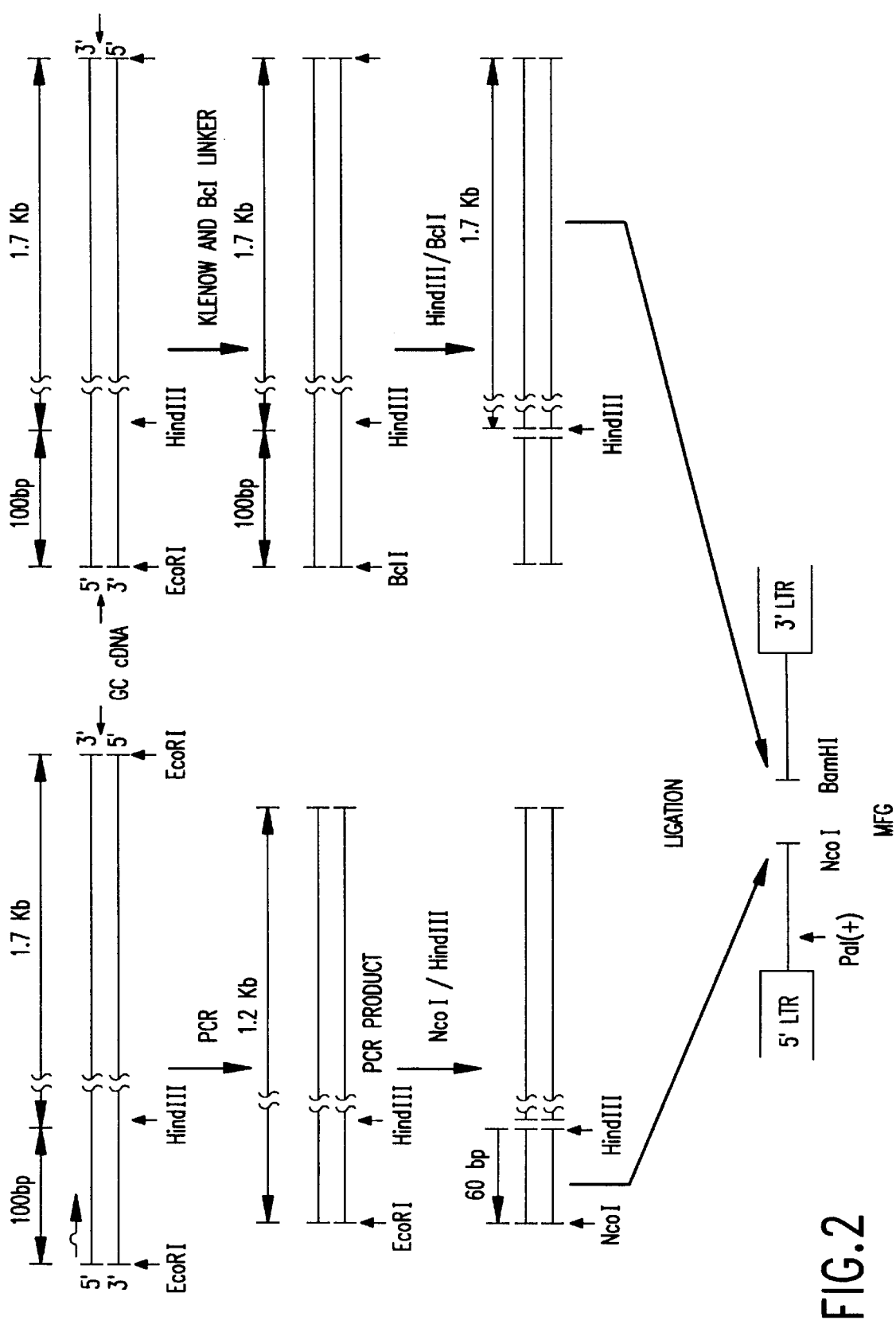
FIG. 2 Shows the strategy for the assembly of the MFG-GC vector of the present invention.
Figure 3:
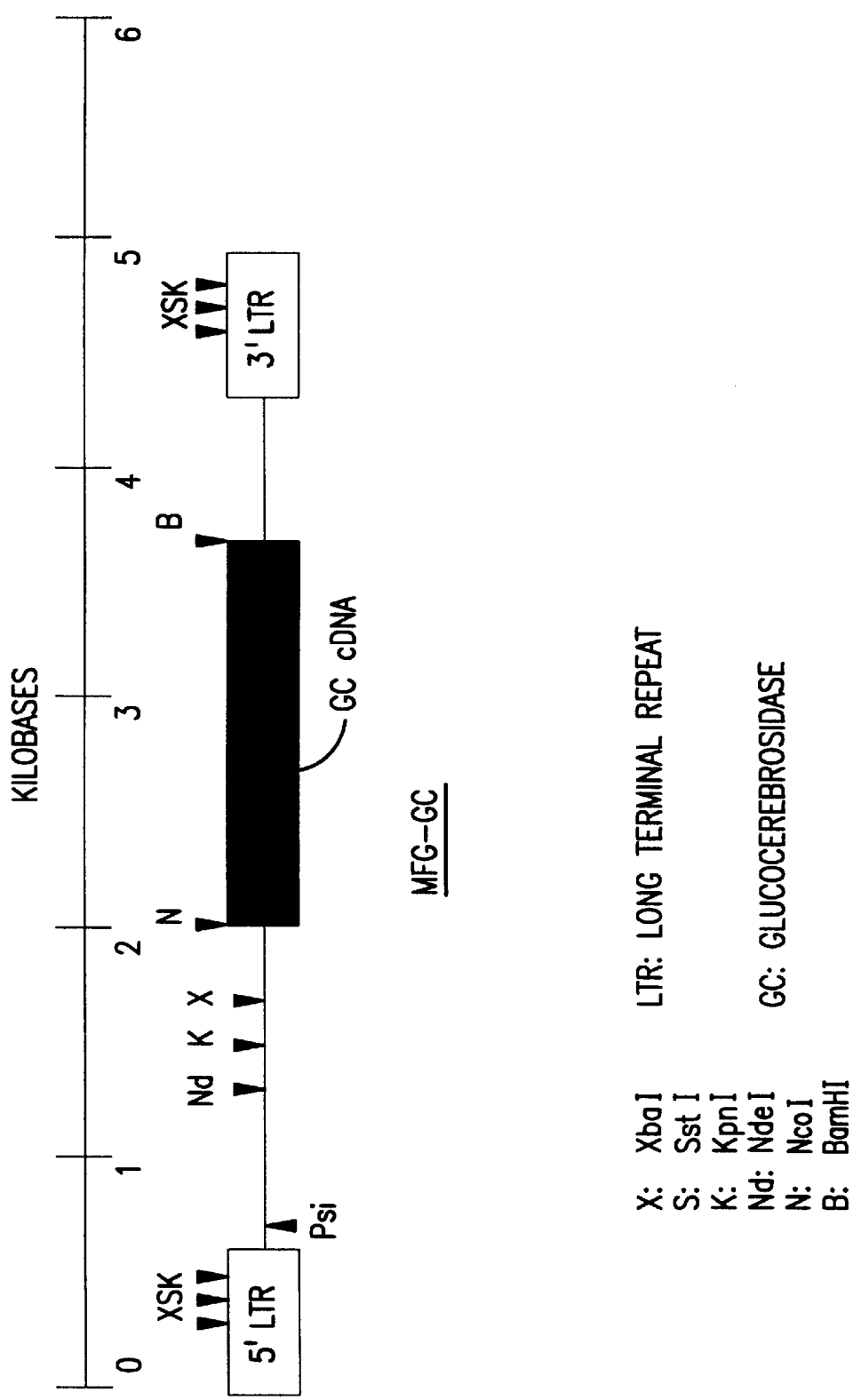
FIG. 3 Shows the structure of the MFG-GC provirus.

The strategy for the construction of the MFG-GC vector is shown in FIG. 2. In order to create an Nco I site in the position of the start codon (ATG) of GC cDNA, polymerase chain reaction (PCR) was carried out with the primers shown in FIG. 2. The sense primer was made with a one base pair mismatch to create an Nco I site. The antisense primer was located downstream of a Hind III site. PCR was carried out using a thermal cycler (Perkin Elmer, Norwalk, Conn.) according to the manufacturer's protocols. The resulting PCR product was then cut with Nco I and Hind III and a 60 bp fragment was isolated using 4% NuSieve™ agarose gel (FMC Bio Products, Rockland, Me.). On the 3' side of the GC cDNA, an Eco RI fragment of GC cDNA was isolated and the terminus was filled in with dNTP's by the Klenow fragment (Boehringer Mannheim, Gmblt, Germany) to create a blunt end. A Bcl I linker was ligated to this fragment in the usual manner and was digested with Hind III and Bcl I. The resulting 1.7 Kb Hind III/Bcl I fragment was isolated from 1% low melting point agarose gel. The 60 bp Nco I/Hind III fragment and 1.7 Kb Hind III/Bcl I fragment were then ligated to the Nco I/Bam HI site in the MFG vector. The construction was confirmed by DNA sequencing according to the method of Sanger, F., et al. *Proc. Natl. Acad. Sci. USA* 74:5463 (1977), which revealed no PCR errors. The structure of the MFG-GC provirus is shown in FIG. 3.

Alternative constructions of replication defective retroviral vectors containing the GC gene and which are capable of transducing and long term expression of the GC gene are also within the scope of the present invention. One example incorporates a Neo® gene into the MFG-GC vector for the purposes of selection of transduced cells and may be used to select an enriched population of human cells carrying the therapeutic GC gene.

Isolation of Virus Producing Cells and Titering

The psi-cre producer line, as described by Danos, O., et al., *Proc. Natl. Acad. Sci. USA* 85 6460 (1988), and NIH 3T3 murine fibroblast cells (ATCC, Rockville, Md.) were cultivated in Dulbecco's modified Eagle's medium (DMEM) (Gibco, Grand Island, N.Y.), supplemented with 4.5 g/l glucose, 3.7 g/l NaHCO$_3$, 10% heat inactivated calf serum, 100 U/ml penicillin (Gibco), and 200 µg/ml L-glutamine (Gibco). MFG-GC was co-transfected with pSV2Neo to Psi-cre, because no dominant selectable marker is present in this construct. After selection by the neomycin analog Geneticin G418 (Gibco) (400 µg/ml), 30 clones were isolated and grown to near confluence in 100 mm dishes. The culture medium of these clones was used as the virus source. As a target cell for titering, NIH 3T3 murine fibroblast cells were used. The virus containing medium was added to 3T3 cells and grown to a density of 4×10$^4$ in 6 well dishes. Polybrene (Sigma, St. Louis, Mo.) was also added to the medium at a concentration of 8 gg/ml to facilitate entry of the virus to the cells. After a 2 hour incubation at 37° C., the virus containing medium was removed and fresh medium without virus was added. Following a 48 hour incubation at 37° C., the cells were harvested and analyzed by measurement of GC activity, Western blots, and Southern blots.

To provide a comparison with the MGF-GC vector of the present invention, another retroviral vector, N2-SV-GC was constructed and used to infect 3T3 cells and bone marrow. The N2-SV-GC vector was constructed by inserting a normal GC cDNA under control of the SV40 early region promoter into the Moloney murine leukemia virus-derived N2 vector, as described by Nolta, J. A., et al., *Blood* 75, 3:787 (1990). In order to isolate virus producing cells and titer the virus, N2-SV-GC constructs were transfected to the ecotropic packaging line, psi-cre, using the calcium phosphate co-precipitation method of Chen, C., et al., *Mol. Cell Biol.* 7:2745 (1987). NIH 3T3 target cells infected by N2-SV-GC were selected by G418 (400 mg/ml). After 2 weeks, the G418 resistant colonies were counted to determine the virus titer. Southern blots of non-selected cells were performed for comparisons of titers with the MFG-GC vector.

EXAMPLE 2

TRANSFER OF HUMAN GC GENE TO 3T3 CELLS BY MFG-GC VECTOR

GC Enzymatic Assay

NIH 3T3 murine fibroblasts were infected with either MFG-GC or N2-SV-GC virus-containing supernatants as described above and selected in 0.5 mg/ml G418 for 1 week. Fibroblasts for GC enzymatic assay were trypsinized, washed twice with Hank's Buffered saline solution (HBSS), and lysed in "sonication buffer" (50 mmol/l potassium phosphate buffer, pH 6.5 with 0.25% Triton X-100). Samples were sonicated for two 30-second pulses at 40 watt-seconds and centrifuged at 12,000 RPM for 2 minutes at 4° C. The protein concentrations of the cleared sonicates were determined with the Pierce BSA kit (Pierce, Rockford, Ill.) using bovine serum albumin (BSA) for construction of a standard curve.

GC enzymatic activity was measured by the method of Ohashi, T., et al., *J. Biol Chem.* 266:3661 (1991), the disclosure of which is incorporated herein by reference, with the synthetic fluorogenic substrate 4-methylumbelliferyl-β-D-glucopyranoside (4MU-glc) (Sigma, St. Louis, Mo.). The reaction mixture (200 µl) contained 5 mM 4MU-glc, 0.1M citrate phosphate buffer (pH 5.4), 2.1 mM Triton X-100, 0.1% bovine serum albumin, and 3.5 mM sodium taurocholate. After incubation of each cell lysate with the substrate for 30 minutes at 37° C., reactions were terminated by the addition of 3.8 ml of 0.17M glycine carbonate buffer (pH 10.4). The 4-methylumbelliferone (4MU) that had formed was measured fluorometrically. Units of GC activity were expressed as nanomoles of 4MU substrate produced/hour/mg protein. All values represent the average of duplicate measurements.

The enzymatic activity of MFG-GC infected NIH 3T3 cells with the highest activity (best 5 out of 20) are shown in Table 1 below. All of these cells exhibit approximately 5 to 10 times higher activity than non-infected NIH 3T3 cells.

TABLE 1

| Cells | GC Activity |
|---|---|
| GC# 1 | 1392 |
| GC# 4 | 2356 |
| GC# 5 | 1364 |
| GC# 25 | 1261 |
| GC# 31 | 1841 |
| NIH 3T3 | 250 ± 9* |

Activity was expressed as nmol/h/mg protein
*: Mean ± SD of three separate determinations Western Blot Analysis Cells and tissues of interest were lysed in 50 mM potassium phosphate buffer (pH 6.5) containing 0.25% Triton X-100 either by sonication or homogenization using 5 a Dounce type homogenizer. 100 μg of protein was applied to a 7.5% SDS-polyacrylamide gel and electroblotted onto a nitrocellulose membrane. The human GC protein was detected by immunostaining using monoclonal antibody 8E4 and alkaline phosphatase conjugated anti-mouse Ig-G goat antibody (BioRad, Richmond, Calif.). The 8E4 monoclonal antibody is specific for human GC and does not cross react with endogenous mouse GC. See, Barnevald, R. A., et al., *Eur. J. Biochem.* 134:585 (1983), and Ohashi, T., et al., *J. Biol. Chem.* 266:3661 (1991).

Figure 4:
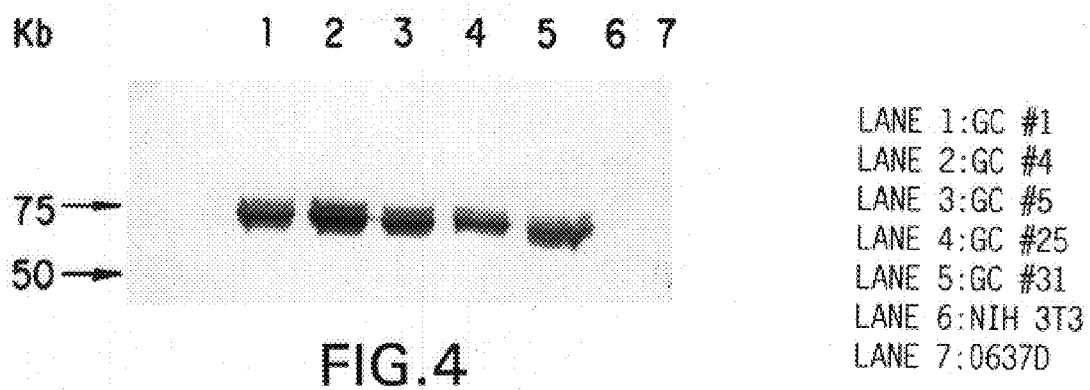
FIG. 4 Photograph of a Western blot of immunoreactive human GC protein resulting from infection of NIH 3T3 murine fibroblast cells with MFG-GC- described in Table 1 (lanes 1–5) as compared to uninfected NIH 3T3 ells (lane 6) and human fibroblast 0637D cells (lane 7).

The results of the Western blot analyses are shown in FIG. 4. Lanes 1–5 contained immunoreactive expression product from the five samples of MFG-GC infected NIH 3T3 cells shown in Table 1. Lane 6 contained non-infected NIH 3T3 cells and lane 7 contained a human fibroblast line, 0637D (ATCC accession number as a control which is an SV40 Ori transformed normal human fibroblast that carries one copy of the GC gene pet cell. Because of the very strong signal for GC in the 3T3 target cells, the Western analysis was adjusted so that the 0637D signal was just at the limit of detection in order to estimate expression in the target cells. The expression in the targets was estimated to be about 5–10 times that observed in the control. The blots showed the expressed protein was of the expected size range (59–66 Kd).

Southern Blot Analysis

Southern blot analyses of DNA from MFG-GC infected cells were carried out as follows. Genomic DNA was extracted by proteinase K treatment, phenol extraction and ethanol precipitation, according to methods known in the art. The DNA was digested with Sst I which cut in both LTR regions in the constructs and produced a 4.3 Kb and 4.9 Kb band from the MFG-GC and N2-SV-GC vectors, respectively. The digested DNA was separated in 1% agarose and blotted onto a nitrocellulose membrane. Known amounts of plasmid DNA from MFG-GC and N2-SV-GC were run on the same gel and the vector copy number per genome was estimated by comparison of band intensities. Human GC cDNA was used as the probe. Hybridization and washing were performed using standard techniques. See, Ausubel, F. M., et al., Eds. *Current Protocols in Molecular Biology* Wiley-Interscience, New York (1995).

Figure 5:
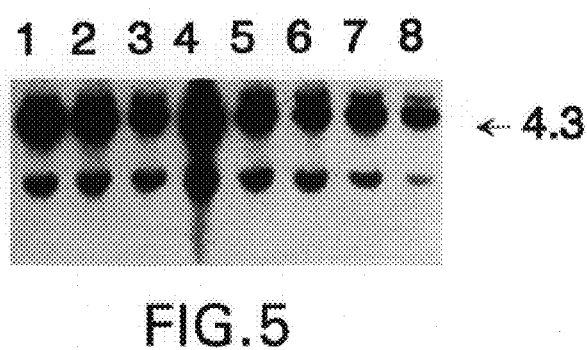
FIG. 5 Photograph of a Southern blot of NA from MFG-GC infected NIH 3T3 fibroblasts and probed with human $^{32}$P-GC-cDNA. Lanes 1–3 are controls containing 1 pg, 5 pg, and 10 pg of MFG-GC, respectively, and lanes 4–8 contain DNA from the MFG-GC infected 3T3 cells described in Table 1.

FIG. 5 shows the results of Southern blot analyses performed as described above with the same five MFG-GC infected samples used in the Western blots (lane 4-GC #31; lane 5-GC #25; lane 6-GC #5; lane 7-GC #4; lane 8-GC #1), and MFG-GC standards in varying amounts (lane 1=2 pg; lane 2=5 pg; and lane 3=10 pg). The results reveal approximately 1–2 copies of GC per cell. This expression correlates well with the results of the Western blots described above.

FIG. 6 shows the results of Southern and Western blot analyses and an enzymatic assay for 3T3 cells infected by MFG-GC and N2-SV-GC showing the enhanced expression of GC for cells infected by MFG-GC as compared to N2-SV-GC.

In the following example, long term bone marrow cultures (LTBMC) were established in order to study gene transfer by MFG-GC and expression of the GC gene.

EXAMPLE 3

TRANSDUCTION AND EXPRESSION OF THE HUMAN GC GENE IN LTBMC

Establishment and Growth of Murine LTBMC

Bone marrow was harvested from 6- to 8-week-old C57BL/6J (B6) mice (Jackson Laboratories, Bar Harbor, Me.) by flushing the marrow cavities of the femurs and tibiae from the donors with cold RPMI medium containing penicillin (100 U/ml) and streptomycin (100 μglml) (Gibco). The cells were washed once with RPMI-10% FCS, resuspended in Iscove's modified Dulbecco's medium (IMDM) (Gibco), and viable cell numbers were determined with trypan blue. Prior to placing the marrow into culture, it was infected by either the MFG-GC or N2-SV-GC vector as described below in Example 4 in the protocol for infecting marrow to be used for bone marrow transplantation. To establish LTBMC, $1 \times 10^7$ nucleated cells were placed into T25 vented filter-top flasks (Costar, Cambridge, Mass.) in complete bone marrow medium (CBMM). CBMM is IMDM, 30% HI-FCS (Gibco); 1% deionized bovine serum albumin (BSA) (Sigma); 106 mol/l hydrocortisone (Abbott Labs, N. Chicago, Ill.); $1 \times 10^4$ mol/l 2-mercaptoethanol (Sigma); 2 mmol/l glutamine (Gibco); 100 U/ml penicillin (Gibco), 100 μg1ml streptomycin (Gibco); and hematopoietic growth factors provided as 5% (vol/vol) of IMDM-20 conditioned by WEHI-3B (WEHI-CM) (gift of Dr. Sallie Boggs, University of Pittsburgh, Pittsburgh, Pa.) and 5% (vol/vol) of IMDM-20 conditioned for 7 days by murine spleen cells stimulated with 2.5 μg/ml poke weed mitogen (PWM-CM) (Gift of Dr. Sallie Boggs). To maintain the LTBMC, half of the culture medium and nonadherent cells were replaced with fresh CBMM every 5 to 7 days. These LTBMC were maintained for over 10 months with sustained production of hematopoietic progenitors (assayed in a CFU-GEMM colony assay) and mature blood cells (determined by Wright-Geimsa staining (Fisher, Pittsburgh, Pa.) of cytocentrifuge preparations).

Analysis of LTBMC Infected by MFG-GC

Southern blot, Western blot, and enzymatic analyses of murine LTBMC were performed and the results are summarized in FIG. 6. It is shown that the MFG-GC vector was capable of infecting LTBMC very efficiently and allowed efficient transcription and translation of the GC MRNA. The Southern analyses show that the infection of these various cells approached 100%. The activity of the enzyme in transduced cells was approximately five to thirty (5–30) fold above the background and continued at that level for more than 5 months in culture.

In the following example the ability of MFG-GC and N2-SV-GC to infect and be expressed in CFU-S was compared.

EXAMPLE 4

Analysis of CFU-S for Transduction Efficiency and Expression of the Human GC Gene Lethally irradiated mice that received $1 \times 10^5$ donor bone marrow cells infected with MFG-GC or N2-SV-GC were studied 12 days after bone marrow transplantation for spleen colonies as described below in Example 5. All animals survived the transplantation. Each mouse had a spleen that was 8–10 times the weight of a normal spleen and was essentially replaced by confluent colonies of bone marrow origin.

A piece of spleen containing at least one colony was prepared from each mouse. These spleen fragments were analyzed by Southern blotting of genomic DNA cut with Sst 1 which released the MFG-GC provirus as a 4.3 Kb fragment which was identified with a cDNA probe specific for human GC. Western blots and enzymatic assays of spleen colonies were performed as described above. All five of the spleens from mice receiving MFG-GC infected bone marrow were positive for the human GC gene as were all five spleens from mice receiving the N2-SV-GC infected bone marrow. These results are summarized in FIG. 6.

Western blot analysis of immunoreactive human GC protein expressed in spleen colonies of mice sacrificed 12 days after transplantation with bone marrow infected by the MFG-GC vector was performed.

Figure 7:
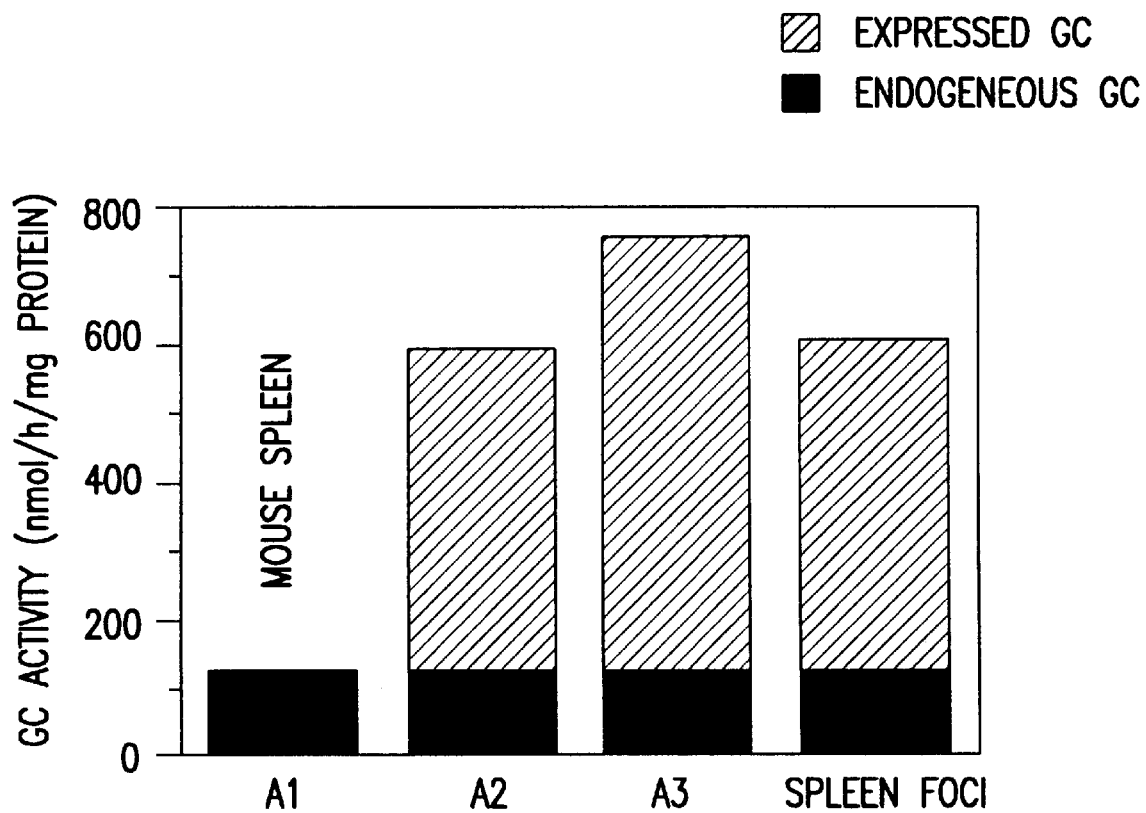
FIG. 7 Graph showing the results of enzymatic analyses of spleen colonies from three mice (A1, A2, and A3) receiving marrow infected by the MFG-GC vector as compared to a colony in the spleen of a mouse transplanted with normal bone marrow.
Figure 8:
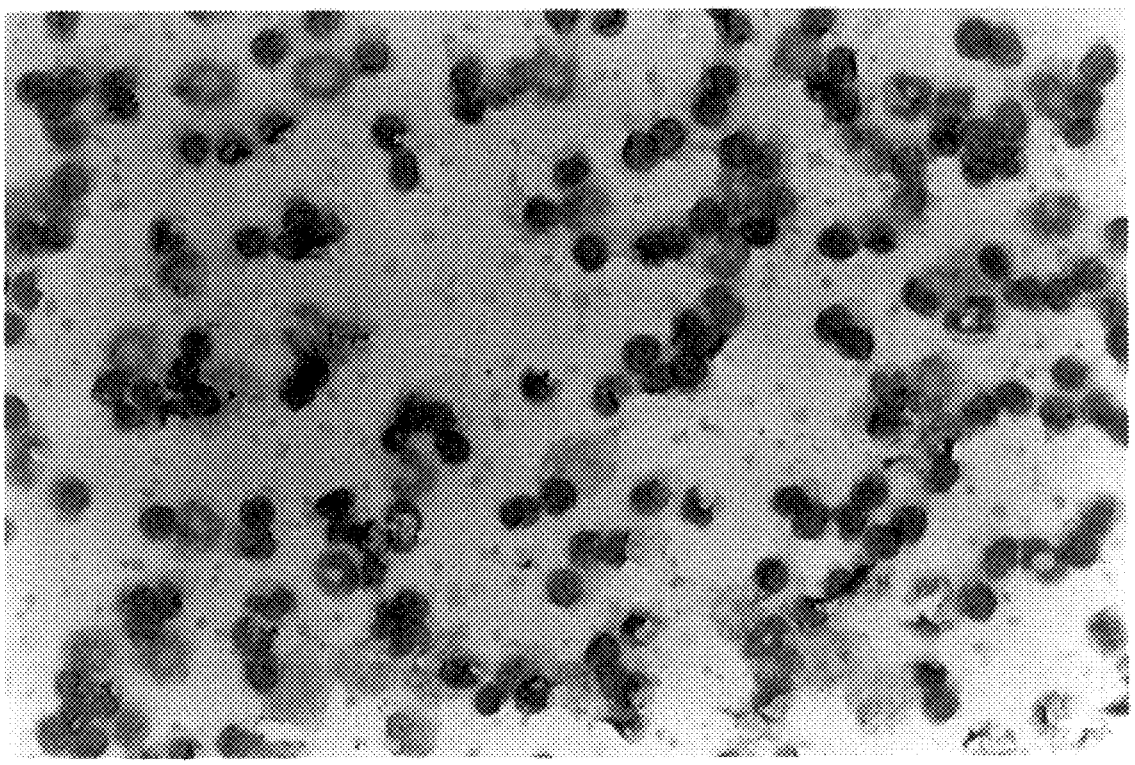
FIG. 8 Photograph of normal mouse leukocytes immunocytochemically stained for human GC protein with monoclonal antibody 8E4.
Figure 9:
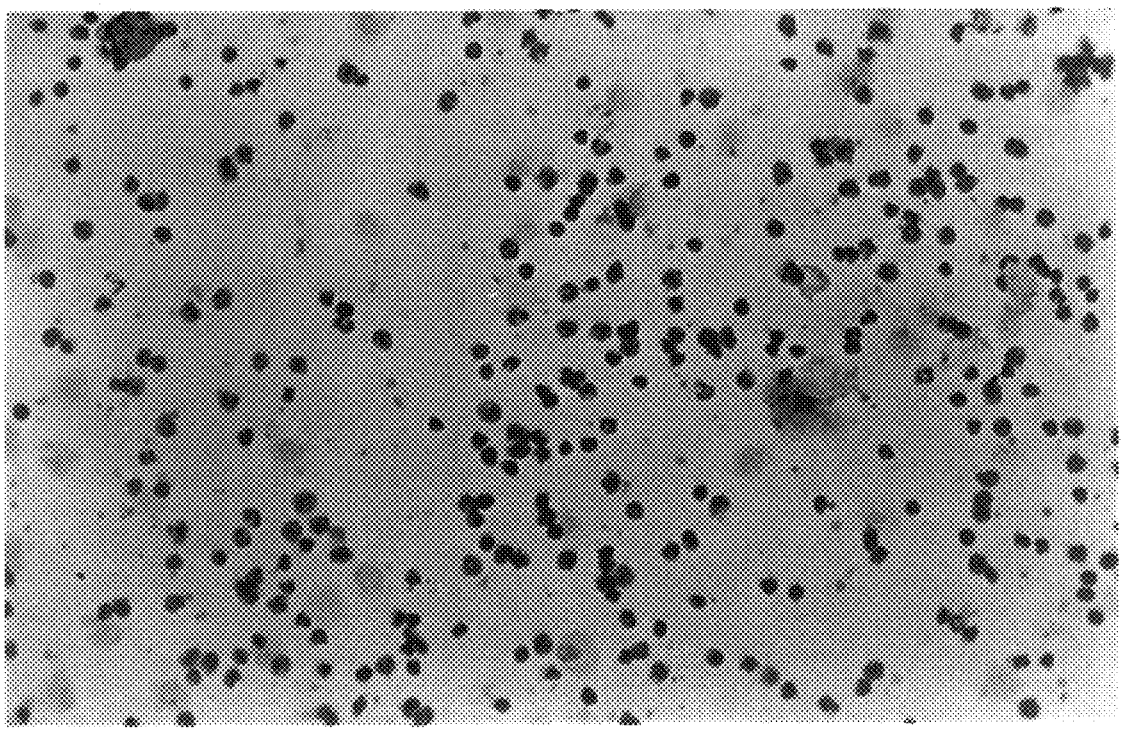
FIG. 9 Photograph of mouse leukocytes immunocytochemically stained for human GC. The cytospin preparation was made from the buffy coat of whole blood drawn from a mouse reconstituted with bone marrow infected with the MFG-GC vector 5 months previously.
Figure 10:
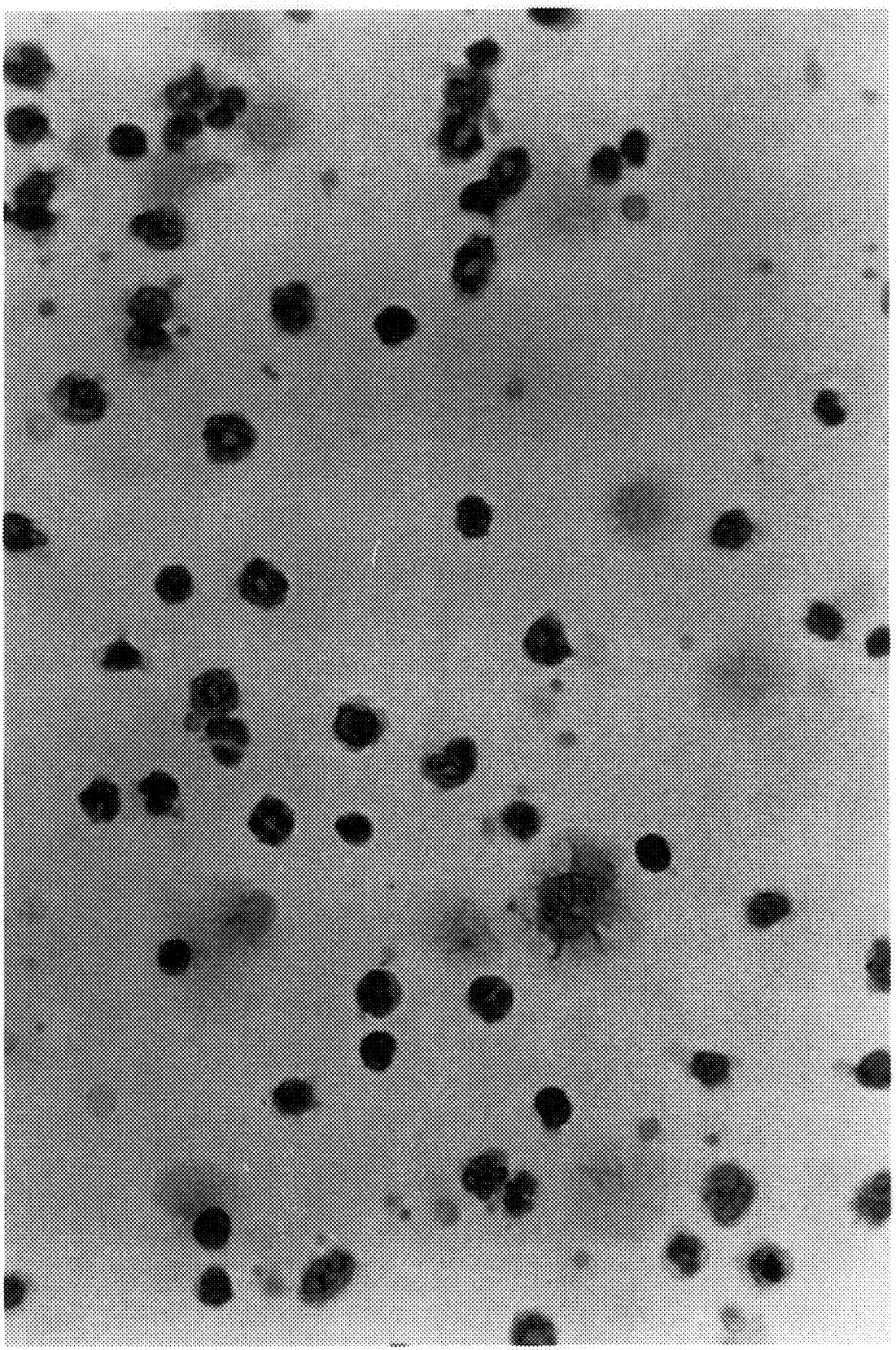
FIG. 10 Photograph of a higher power view of FIG. 9.

There was a positive signal about 4–5 times in intensity to the signal from the human liver control, while the negative control (normal mouse spleen) showed no signal on Western blot. None of the colonies from mice receiving N2-SV-GC infected bone marrow showed detectable expression by Western blot analysis. Enzymatic analyses of spleen fragments from three mice (A1, A2, and A3) receiving marrow infected by the MFG-GC vector and of a control colony of a spleen of a mouse transplanted with normal bone marrow revealed as seen in FIG. 7 that the GC activity in the spleen fragments was 4–5 fold higher than control spleen background.

In the following example the ability of the MFG-GC vector to transfer and express the GC gene in transplanted bone marrow was evaluated.

EXAMPLE 5

EXPRESSION OF GC GENE IN PROGENY OF TRANSPLANTED BONE MARROW

Bone Marrow Transplantation

The ability of the MFG-GC vector to infect and express the GC gene in the progeny of transplanted murine bone marrow was determined using the protocol of Bodine, D. M., et al., *Exp. Hematol.* 19:206 (1991).

Bone marrow cells were harvested from the limbs of C57BL/6J-Gpi-$1^a$ Hbb$^d$ (HW-80) female mice (Jackson Laboratories) 3 days after injection with 5-fluorouracil (5-FU) (150 mg/kg body weight). Bone marrow cells were precultured for 2 days in Fisher's medium supplemented with 15% fetal calf serum, 2 mM L-glutamine, 100 U/ml penicillin, 100 μg/ml streptomycin, and cytokines. Stem cell factor was provided by Dr. Chris Zsebo (Amgen, Calif.) and was used in both preculture and coculture procedures. Initially, 5% conditioned medium from WEHI-3B cells and 5% conditioned medium from poke weed mitogen stimulated spleen cells was used as the source of cytokines. Preculture of the bone marrow cells was followed by 2 days of co-culture with 20 Gy irradiated viral producer cells (psi-cre) in DMEM supplemented with 10% calf serum, 100 U/ml penicillin, 100 μg/ml streptomycin, polybrene (8 mg/ml), and cytokines. In later experiments, recombinant IL-3 (Genzyme, Cambridge, Mass.) and IL-6 (gift of Dr. Zsebo) was used instead of conditioned medium. After coculture, lethally irradiated mice (Gpi-$1^b$) were injected with $2\times10^6$ bone marrow cells for long term hematopoietic reconstitution studies or $1-2\times10^5$ cells for primary day 12 CFU-S assays. Mice were irradiated with 9.5 Gy of radiation. For secondary recipient studies, BM from the primary recipient was collected and $10^7$ cells were injected into lethally irradiated recipients for long term reconstitution studies. For secondary CFU-S studies, $10^6$ cells were transfused into the recipients.

Transplanted animals were maintained to evaluate the infection and expression of the GC gene in cells present in the bone marrow capable of long term reconstitution of the bone marrow of the recipients. The success of engraftment of transplanted bone marrow was monitored by the differences in the GPI isoenzymes of the donor and recipient animals, as described below.

Glucose Phosphoisomerase I (GPI) Isozyme Assay

Hematopoietic reconstitution of the recipient mice, i.e., the extent of engraftment and reconstitution by donor bone marrow (BM) cells of irradiated recipient mice, was monitored by the difference in the electrophoretic mobility of the GPI isozyme (GPI-$1^a$ and GPI-$1^b$) present in the donor and recipient leukocytes of the mice. Such markers permit the estimation of the success of engraftment of the donor marrow.

GPI isozymes in peripheral blood leukocytes were separated and analyzed using cellulose acetate electro-phoresis followed by enzymatic activity staining according to the methods of Eppig, J. J., et al., *Nature* 269:517–520 (1977). Donor mice were female (HW-80) mice (Jackson Laboratories) and the recipient mice were C57BL/6J-Gpi-$1^b$ (Jackson Laboratories). The results of the GPI isozyme assay indicated that all recipient animals in this study had >90% donor cells.

To determine if the engrafted cells were transduced and expressed human GC in their progeny, estimations were made of peripheral blood cells using an immunoperioxidase stain specific for the human gene product using the Vecta stain ABC kit (Vector, Burlingame, Calif.) according to the manufacturer's instructions. Purified BE4 was used as the primary antibody. The same method was used to stain cultured macrophages as described below. Cytospin preparations of peripheral blood were fixed and incubated with the human GC specific MAb 8E4. The results of these studies on animals at 5 months after bone marrow transplantation are shown in FIGS. 8–11. The normal BM in FIG. 8 has no staining, whereas in FIGS. 9 and 10 (higher power of FIG. 9) the peripheral leukocytes of a mouse reconstituted with MFG-GC infected marrow five months previously showed the presence of human GC enzyme protein as red color. Approximately 80% of the white blood cells were positive and several different cell lineages appeared to be expressing the human gene.

PCR analysis for the human gene was performed on the bone marrow (BM) and peripheral blood (PB) of three long term reconstituted mice. The analysis revealed a 192 bp product from the MFG-GC provirus from the bone marrow and peripheral blood of each long term reconstituted mouse.

EXAMPLE 6

Long Term Reconstitution Studies

Comparisons of the two retroviral vectors N2-SV-GC and MFG-GC were performed based on Southern and Western blots and enzymatic activities in 3T3 cells, spleen foci (CFU-S), LTBMC, and tissues of mice surviving for longer than 4 months after reconstitution with bone marrow infected by co-cultivation with the $N_2$-SV-GC and MFG-GC producer lines. Tissues analyzed by Southern and Western analysis and by enzymatic activity included bone marrow, spleen, liver, lung, thymus, and lymph node. Protocols of the Southern and Western analysis and enzymatic assay are described above, as well as the protocol for preparing and reconstituting bone marrow for long term recipients.

Figure 12:
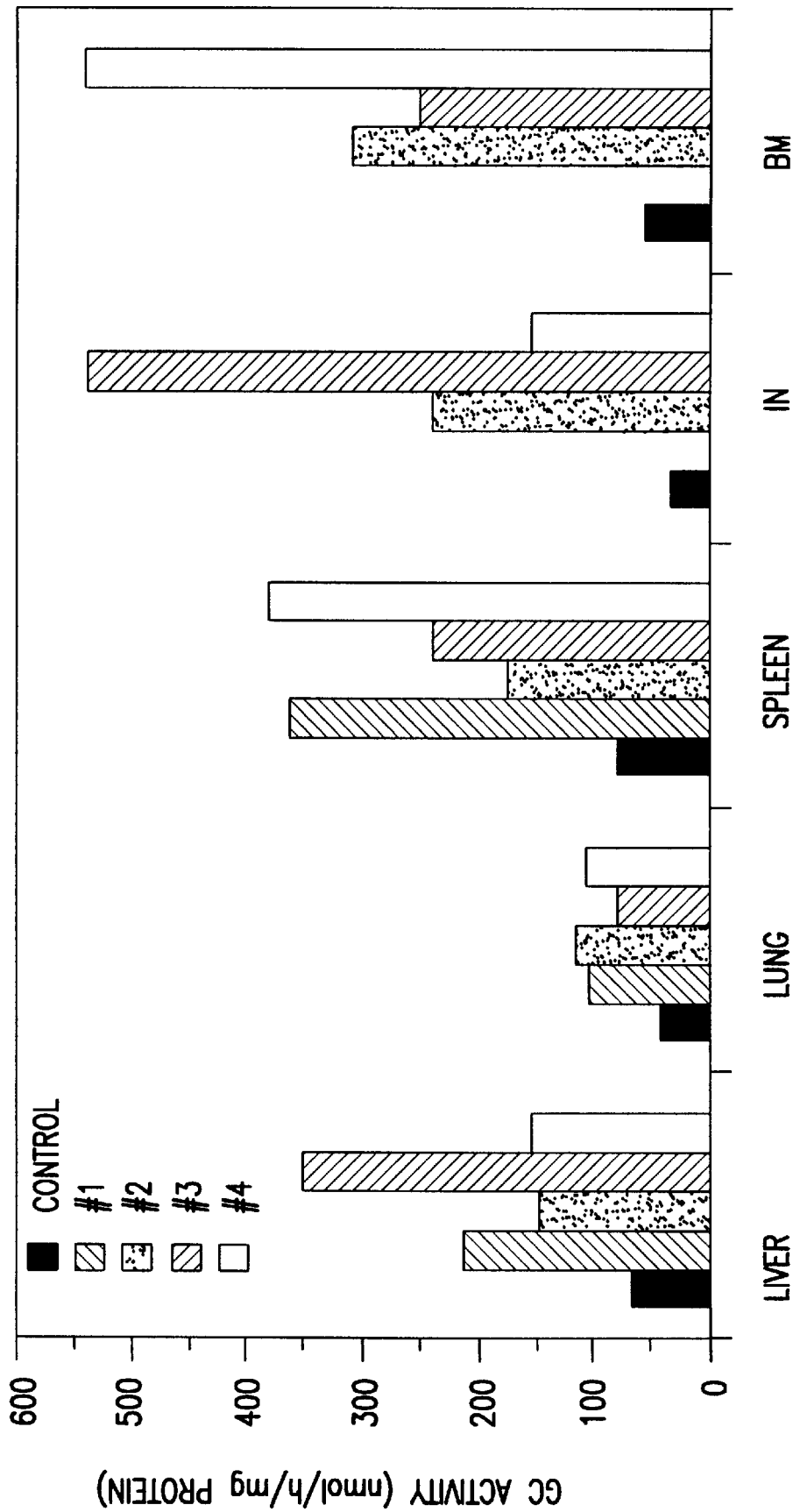
FIG. 12 Graph showing GC activities in the tissues (liver, lung, spleen, lymph node (LN), and bone marrow (BM)) of four mice surviving longer than four months after reconstitution with bone marrow infected by co-cultivation with MFG-GC, with the control being the activity present in the respective tissues of normal mice.

Eleven HW 80 mice were used in the studies-nine for study of MFG-GC and two for N2-SV-GC study. The data are summarized in FIG. 11. The enzymatic activities of the tissues of four mice reconstituted with MFG-GC infected bone marrow are shown in FIG. 12. The hematopoietic tissues (spleen, bone marrow, thymus, and lymph node) from those animals showed GC activities that were in the same range as spleen colonies and consistently several fold higher than the activity of control tissues. The hematopoietic tissues reconstituted by N2-SV-GC infected bone marrow showed little or no increase above the control activities. These results are consistent with the activity data on spleen colonies shown in FIG. 6. From the Southern analysis of hematopoietic tissues it can be seen that both vectors are equally efficient in infecting early progenitors capable of long term reconstitution of bone marrow. The copy number was approximately equal, ranging from about 1 to 2 regardless of the gene transfer vector used. The data indicate that the efficiency of transduction approached 100% in cells in bone marrow capable of long term reconstitution.

In addition, the size of the vector recovered from the tissues was uniform for each tissue analyzed and was consistent with the vector used. Restriction with Sst-1 cleaved in the retroviral LTR produced a 4.9 kb fragment from the N2-SV-GC vector and a 4.3 kb fragment from the MFG-GC vector. Thus there appeared to be no large rearrangement of the vector in the long term reconstituted animals.

As indicated above, however, it is clear that the MFG-GC vector is transcriptionally more efficient than the N2-SV-GC. Further, the MFG-GC infected marrow produced cells on a long term basis which comprised the majority of bone marrow derived cells in the spleen, bone marrow, and thymus as well as approximately 1 in 10 cells in the liver.

The data shown in FIGS. 11 and 12 accumulated on non-hematopoietic tissues (liver, lungs) is also informative. These tissues normally receive bone-marrow derived cellular elements on a continuing basis. Under normal physiologic circumstances, bone marrow derived cells in tissue are primarily macrophages and reflect the normal provision of tissue macrophages by the bone marrow. In liver, tissue macrophages (Kupffer cells) constitute approximately 15% of the cells present at any time. See, Barranger, J. A., *N. Eng. J. Med.* 311:101 (1984). If all of the liver macrophages were replaced in the animals by the progeny of transduced early progenitors in the bone marrow, the copy number of the vector in the liver should be about 0.15/cell in long term reconstituted animals. The results herein demonstrate that both the N2-SV-GC and MFG-GC vectors result in a copy number in liver of approximately 0.1/cell. This is consistent with a transduction efficiency approaching 100% as shown from the data derived from hematopoietic tissues. Furthermore, the enzymatic activity of the lung and liver of MFG-GC transduced animals is several fold above background, but is on average less than that of hematopoietic tissues. This is indicative of the lesser number of bone-marrow derived cells present in those tissues and is consistent with the higher enzymatic activities measured in organs that have a higher proportion of bone marrow derived cells (e.g., bone marrow, spleen, and lymph node).

EXAMPLE 7
Transduction and Expression of GC Gene in Macrorhages

Macrophages were cultured from the bone marrow of animals whose bone marrow were reconstituted long term (>4 months) with bone marrow -transduced by either the N2-SV-GC or MFG-GC vector.

The bone marrows were cultured by the method reported by Gregory, S. H., et al., *J. Leukocyte Biol.* 43:67 (1988). Conditioned media containing macrophage colony stimulating factor (M-CSF, also designated as CSF-1) was used to culture the whole bone marrow from mice reconstituted with MFG-GC infected bone marrow and surviving longer than five months. $2 \times 10^5$ bone marrow cells from the long term reconstituted mice were suspended in 20 ml of DMEM supplemented with 4.5 g/l glucose, 3.7 g/l $NaHCO_3$ 10% heat inactivated FBS, 20% heat inactivated horse serum, 20% L-929 cell@ conditioned medium (gift of Dr. Sallie Boggs), 100 U/ml penicillin, 100 $\mu$g/ml streptomycin, 200 $\mu$g/ml glutamine and then cultivated in 100 mm dishes at 37° C. and 5% $CO_2$. The L-929 conditioned medium contained mouse macrophage colony stimulating factor (M-CSF). See, Stanley, E. R., et al., *J. Biol. Chem.* 252:4305 (1977). Such a culture system resulted in essentially pure colonies of macrophages.

Bone marrow cultured with this medium produced pure macrophage cultures that expanded approximately five logs. After 11 days, latex beads were added to the medium to confirm that the adherent cells were of macrophage lineage. The cells were harvested and assayed by measurement of GC enzymatic activity, immunocytochemistry, Western blot, and Southern blot as described previously. The results are described below.

Figure 13:
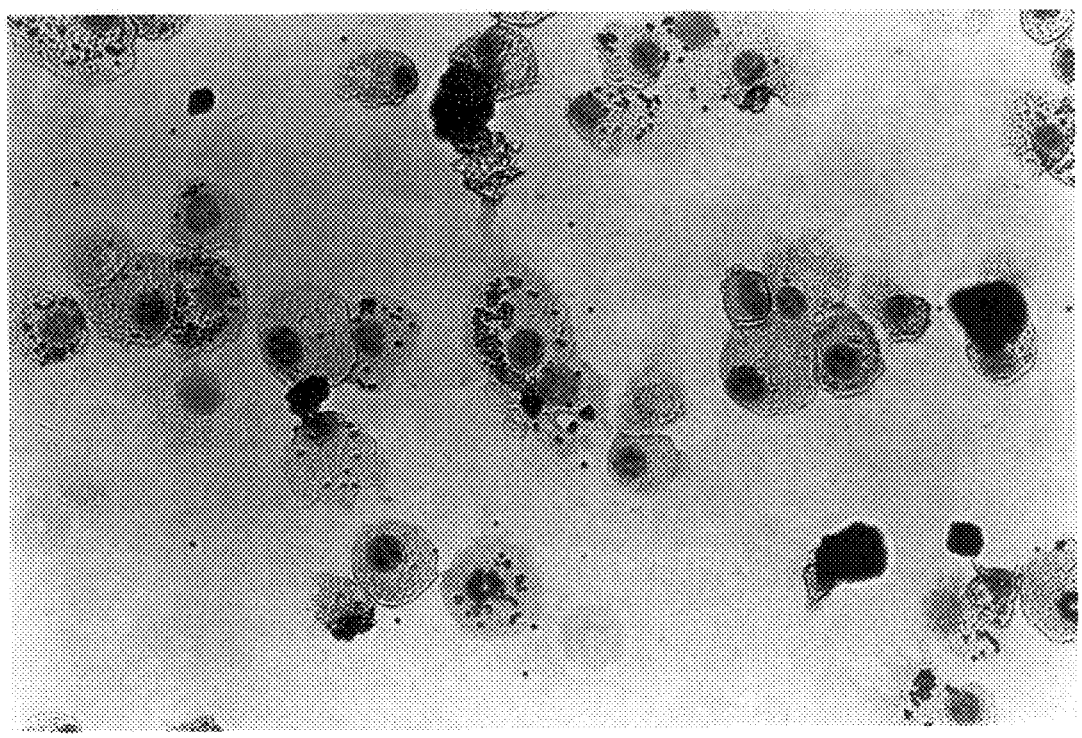
FIG. 13 Photograph of latex bead ingestion by macrophages grown from the bone marrow of long term reconstituted mice that had been rescued with marrow infected with MFG-GC.
Figure 14:
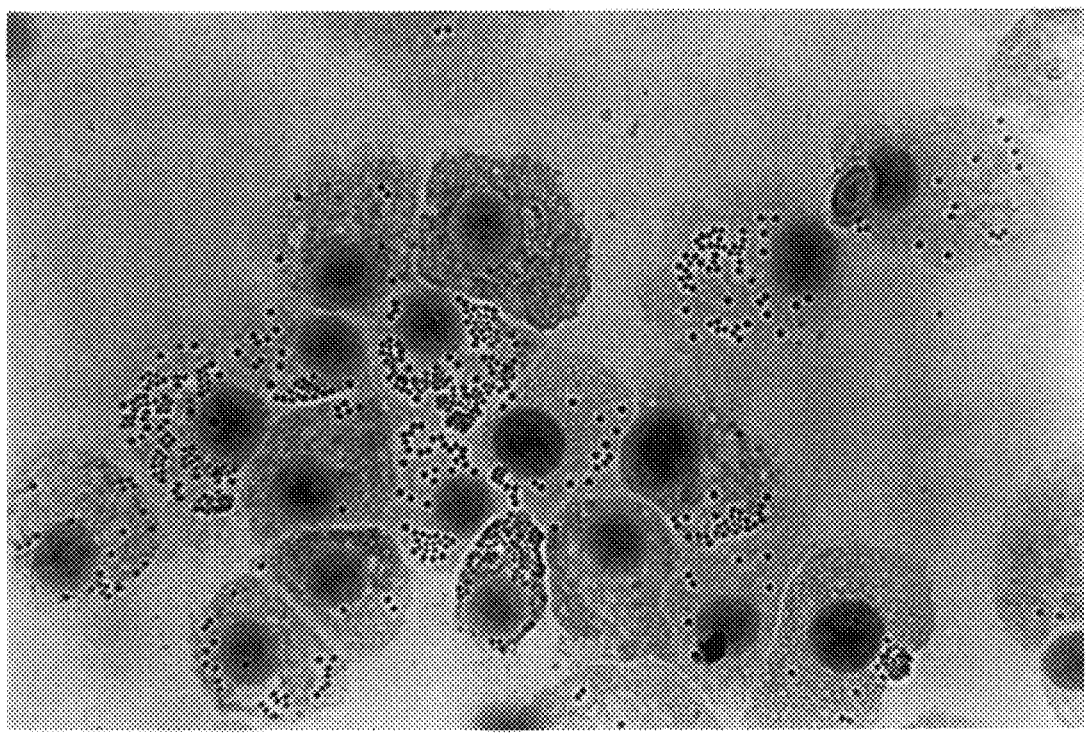
FIG. 14 Photograph of macrophages grown from long term reconstituted mice rescued with marrow infected with MFG-GC five months previously that were immunocytochemically stained for human GC.
Figure 15:
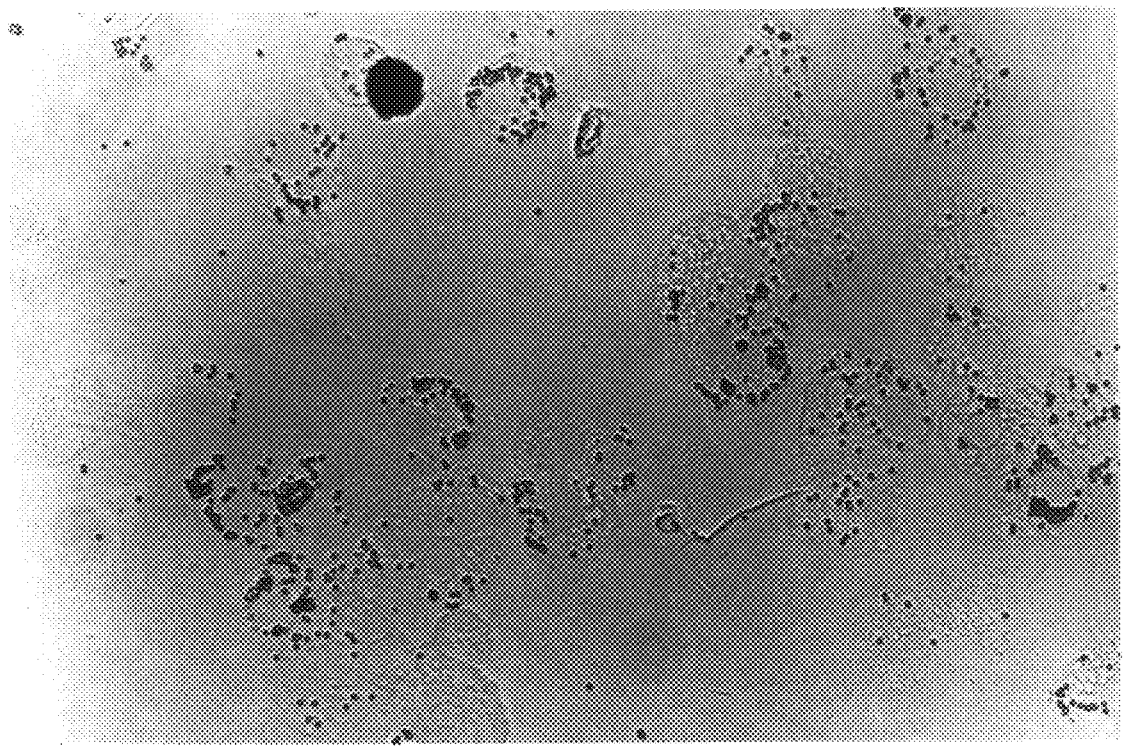
FIG. 15 Photograph of macrophages cultured from normal murine bone marrow that were immunocyto-chemically stained for human GC.
Figure 16:
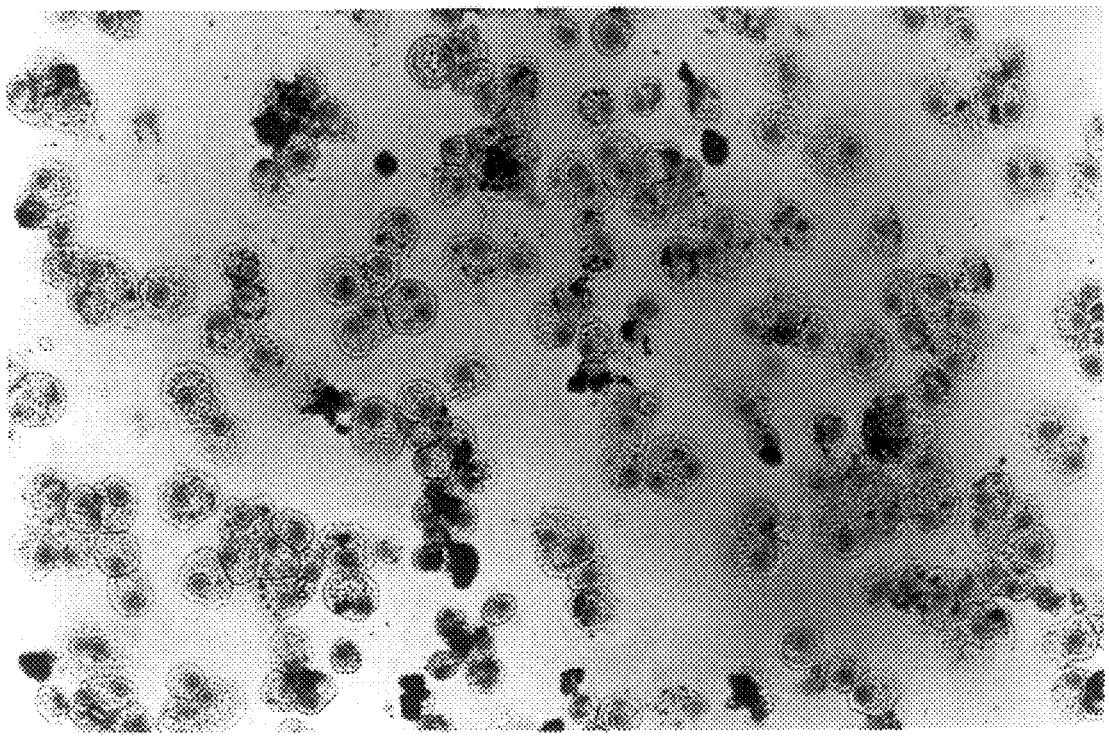
FIG. 16 Photograph of macrophages grown from long term reconstituted mice (>5 mos.) rescued with marrow infected with N2-SV-GC that were immunocytochemically stained for human GC.

Cultures of macrophages established from MFG-GC, control, and N2-SV-GC animals were immunohistochemically stained as described in Example 5 for the human GC gene product. FIG. 13 shows the culture from an MFG-GC reconstituted animal which showed the ability of the cultured macrophages to phagocytose latex beads. This same culture was very positive for expression of the human GC gene product since virtually every cell was stained as seen in FIG. 14. Cultures from a control animal, FIG. 15, and N2-SV-GC reconstituted animal, FIG. 16, were negative for the expressed human gene product. Thus the GC gene was not expressed in macrophages when starting bone marrow was infected by N2-SV-GC.

Figure 17A:
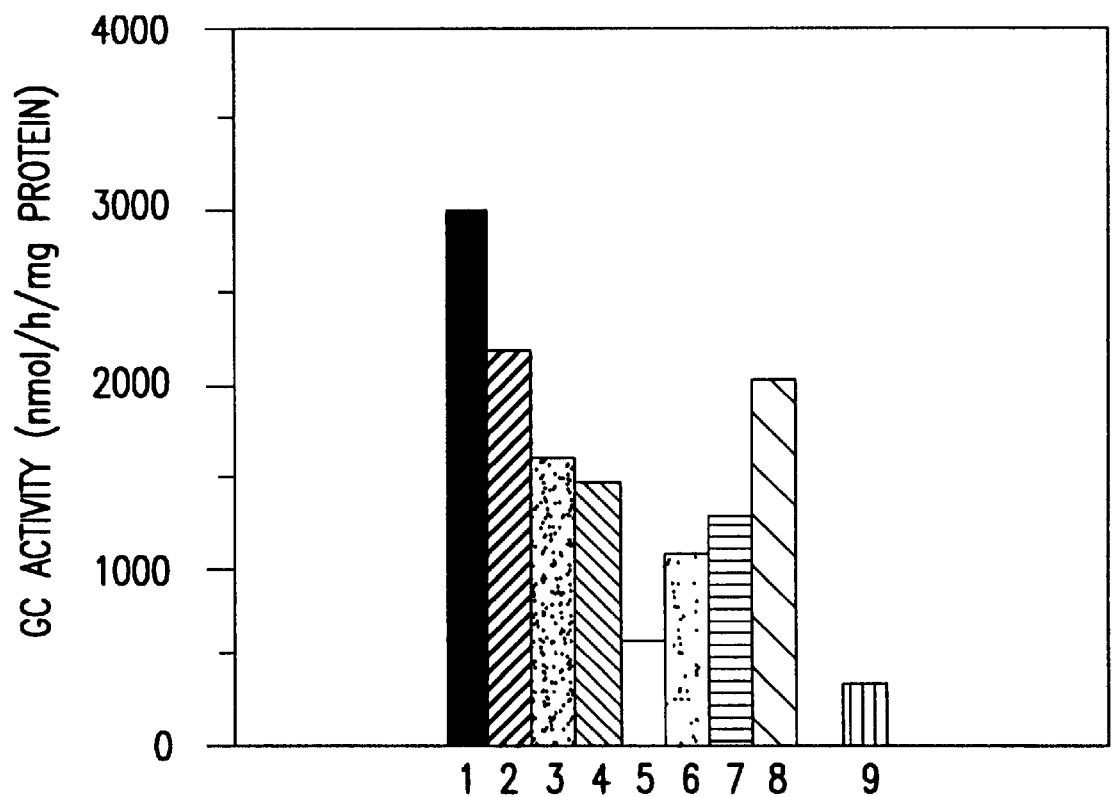
FIG. 17A Graph showing results of enzymatic analyses of macrophages cultured from explanted marrow of eight long term reconstituted mice rescued with marrow infected with MFG-GC (lanes 1–8), and macrophages cultured from a normal control mouse (lane 9).
Figure 17B:
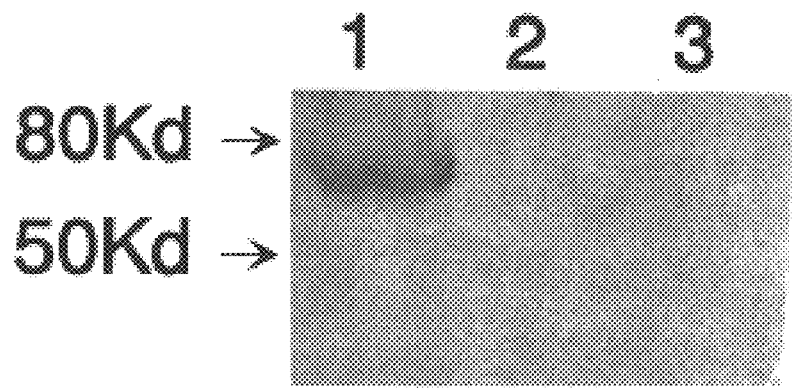
FIG. 17B Photograph of a Western blot of immunoreactive human GC protein expressed in extracts from macrophages cultured from explanted marrow of a long term reconstituted mouse rescued with marrow infected with MFG-GC (lane 1) and in extracts from a control mouse macrophage culture (lane 2).
Figure 17C:
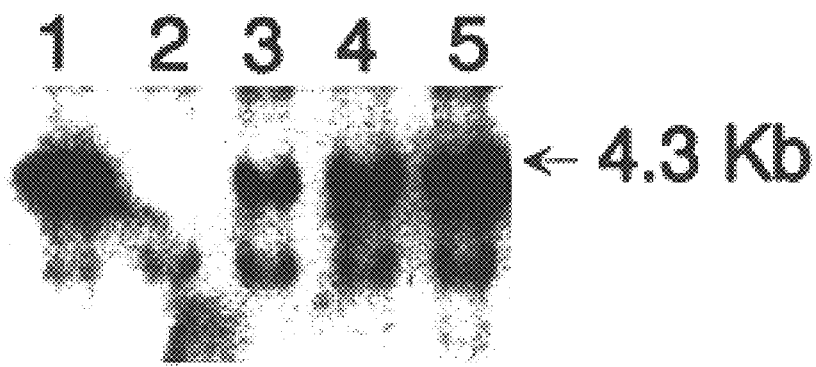
FIG. 17C Photograph of a Southern blot of DNA from macrophages cultured from explanted marrow of a long term reconstituted mouse rescued with marrow infected with MFG-GC (lane 1). Lane 2 is a normal mouse control, and lanes 3–5 contain standards for estimating copy number representing 0.2, 0.5, and 1.0 copies/cell, respectively. The DNAs were probed with human 32P-GC-cDNA.

MFG-GC macrophages cultured from explanted bone marrow obtained from eight different mice reconstituted long term with MFG-GC infected bone marrow and macrophages cultured from a control mouse were assayed for GC enzymatic activity. As seen in FIG. 17A, the enzymatic activity of the MFG-GC macrophages (lanes 1–8) was on average approximately 5 times that of the control macrophage activity (lane 9). Western blot analysis in FIG. 17B of immuno-reactive human GC protein expressed in extracts from macrophages cultured from explanted marrow of a long term reconstituted mouse rescued with marrow infected with MFG-GC (lane 1) and in extracts from a control mouse macrophage culture (lane 2) showed that the protein of the expected size range (59–66 Kd) is expressed by the MFG-GC transduced macrophages (lane 1). In FIG. 17C Southern blot analysis of DNA from macrophages cultured from explanted marrow of a long term reconstituted mouse rescued with marrow infected with MFG-GC (lane 1); a normal mouse control (lane 2); and standards for estimating copy number representing 0.2, 0.5, and 1.0 copies/cell, respectively (lane 3) showed the expected 4.3 Kb band for the DNA from the long term reconstituted animal (lane 1). The DNAs were probed with human $^{32}$P-GC-cDNA. The copy number in these cells was approximately 1/cell.

Such results confirm that the transduction efficiency of the MFG-GC and N2-SV-GC-vectors was very high for early progenitors, approaching 100%. However, as seen in the macrophage studies, MFG-GC is a superior vector for the expression of the GC gene in bone marrow derived macrophages.

Secondary Transplants

Figure 18B:
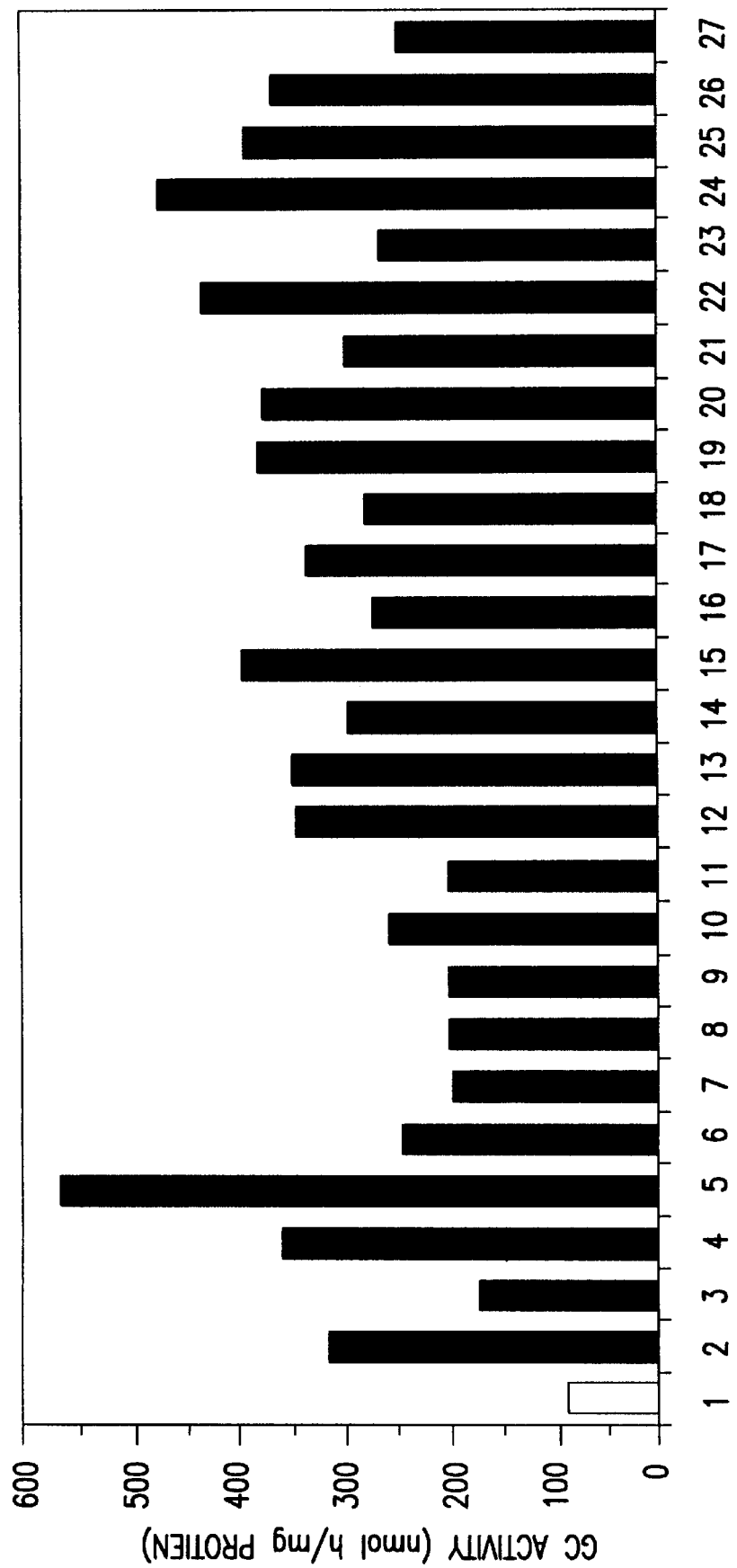
FIG. 18B Graph showing results of enzymatic analyses of 27 individual secondary CFU-$S_{12}$ spleen colonies from three mice that received bone marrow transplants from primary long term reconstituted mice. Lane 1 represents GC activity of an age-related control; and lanes 2–10, 11–19, and 20–27 represent, respectively, spleen colonies from mouse #26, #27, and #28.

As a further measure of the ability of the MFG-GC vector to transduce early progenitors, secondary bone marrow transplantations using bone marrow from long term reconstituted MFG-GC mice were performed. FIG. 18A shows Southern blots of 27 spleen colonies from three mice isolated 12 days post-transplant. DNA was digested with Sst I and probed with full length human GC cDNA. Lanes 1–10 contained DNA from spleen colonies isolated from mouse #26; lanes 11–19 contained DNA from spleen colonies isolated from mouse #27; lanes 20–27 contained DNA from spleen colonies isolated from mouse #28; lane 28 contained genomic DNA isolated from an age-related control; and lanes 29–31 contained standards for estimating copy number (0.2, 0.5, and 1.0 copies/cell, respectively). All twenty-eight foci (28/28) were positive for the human gene. Enzymatic analyses of the same 27 spleen colonies are shown in FIG. 18B. Lane 1 represents GC activity of an lanes 2–10, 11–19, and 20–27 represent, respectively, spleen colonies from mouse #26, #27, and #28, showing GC activity approximately 2–6 times that of the control, thereby providing more evidence that the MFG-GC vector was able to efficiently transduce stem cells.

EXAMPLE 8

Transduction and expression of the Human GC Gene in Normal Human and Gaucher Patient Macrophages (MO)

Human macrophages were cultured from peripheral blood from normal volunteers and patients with Gaucher disease following an approved protocol (IRB # 910505). Blood was collected in 50 cc syringes containing 2.5 ml of Na heparin (1000μ/ml). 6% Dextran was then added in saline solution in an amount that was approximately 10% of the blood volume (to a 50 ml syringe, 5 ml of Dextran was added). The resulting composition was then mixed thoroughly and left undisturbed at room temperature for 40 minutes until a clean separation line was visible between the supernatant and the red blood cell (RBC) layer. Using a bent 18G needle, the supernatant was layered onto Ficoll-Hypaque (Histopague® 1077, Sigma) (F-H). The tubes were then centrifuged for 20 minutes at 530 g (1300–1500 RPM) at room temperature. A mononuclear cell (MNC) layer was easily visible as a white band in the middle of the supernatant. The superantant above the MNC layer was aspirated and disposed. The MNC layer was transferred to a separate tube for washing the Ficoll from the cells. Approximately 20–40 ml of Dulbecco's phosphate buffered saline (D-PBS) (Gibco) (1x) was added to the tubes containing the MNC's, or alternatively, KRP-glucose could be used. The cells were washed thoroughly at least two times, and the pellets were resuspended in culture medium (1640 RPMI (Gibco), 10% FBS, 10% human albumin). The cells were then counted and a viability assay was performed using trypan blue exclusion. Cytospin slides for Wright staining were prepared and the percentages of resultant isolated macrophages and lymphocytes were counted.

In order to culture macrophages, the macrophages from the preceding step were used. The cell count was adjusted to ≈5×106 cells/ml with culture medium (1640 RPMI, 10% FBS, 10% human albumin), and the cells were plated in 35 mm culture dishes (approximately 10 cm$^2$ surface) so that the plating density was between 0.2–0.6×10$^6$ macrophages/cm$^2$. The cells were then incubated at 37° C. in 5% $CO_2$ for 60 minutes, and non-adherent cells were removed after the incubation. Then 1 ml of D-PBS (1x) was gently placed in the dish, and dish was shaken to remove non-adherent cells left in the bottom of the dish. 2 ml of previously warmed culture media was then added to each 35 mm dish, and the cells were then incubated at 37° C. in 5% $CO_2$. The culture medium should be changed only once a week.

In order to infect human macrophages in culture with MFG-GC, the culture medium from the cultured macrophages of the previous step was removed from each culture dish and 1 ml of viral superantant obtained from, the producer cell line described above was added to each culture dish, along with 10 μl of Polybrene (8 μg/ml). The dishes were then incubated at 37° C. in 5% $CO_2$ for 48–72 hours. The plates were then checked to assure an adequate number adherent cells were present. The culture medium containing the viral supernatant was then removed from each culture dish, and each plate was washed with D-PBS (1x), and the D-PBS was removed. Then, 1 ml of Lysis buffer (0.05M K-P, 1% Triton X-100, pH 6.5) was added to each plate, and a rubber policeman was used to detach all cells from the bottoms of each dish. The cell lysates were then transferred to small Eppendorf tubes and placed on ice. The lysates were sonicated and processed for GC specific enzymatic activity and protein assays as described previously.

Figure 19A:
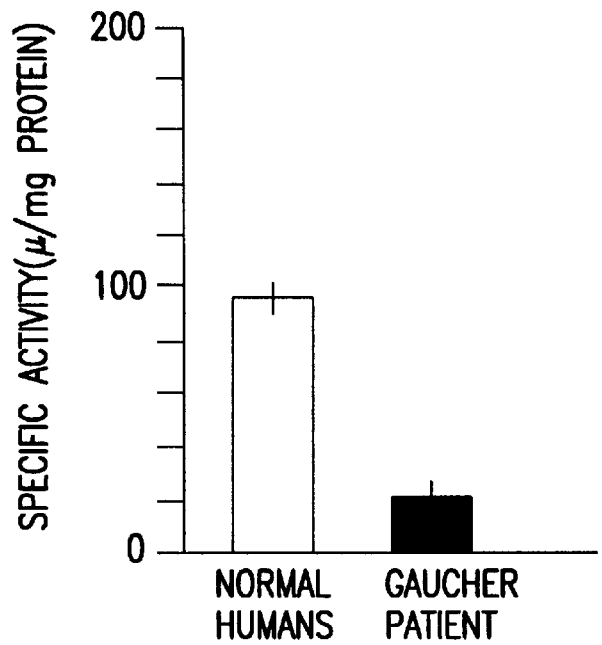
FIG. 19 (Parts A–B) Graph of the GC activity of normal human and Gaucher patient macrophages in culture before (A) and after (B) infection with the MFG-GC vector expressed as nanomoles of 4MU released per hour per mg of cell protein.
Figure 19B:
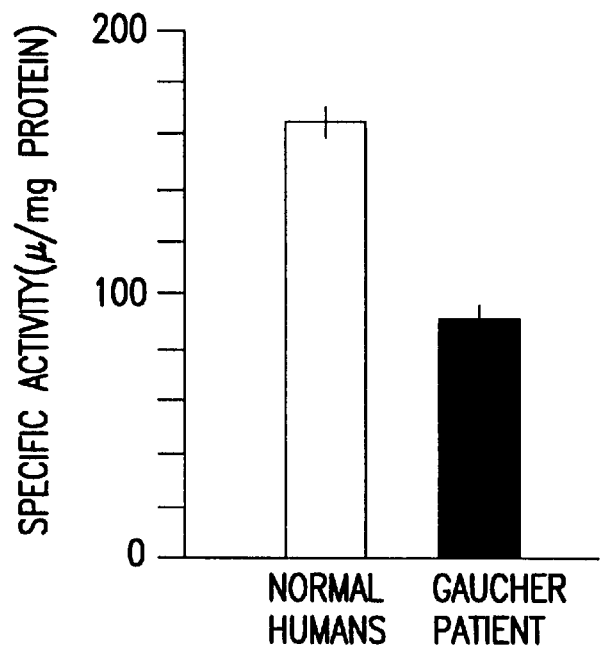

As shown in FIG. 19 the enzymatic activity assays of these cells demonstrated that the MFG-GC vector is able to impart approximately 75 U/mg cell protein to either normal macrophages (A) or the macrophages from patients (B). This increment of enzyme is therapeutically effective to correct the enzymatic deficiency completely in the Gaucher disease patients. The present invention is therefore useful as a method of treating Gaucher disease in human Gaucher patients.

In the following example the absence of replication competent helper virus from viral stocks and tissues of mice transduced with MFG-GC was shown.

EXAMPLE 9

Mobilization Assay for Helper Virus

Supernatants from psi-cre ecotropic producer lines, the PA 317 amphotropic producer lines, and from bone marrow and homogenates of spleen cells from the long term reconstituted animals were assayed by the BAG mobilization method assay for the helper virus. The assay was carried out essentially according to the methods described by Danos, O. *Methods in Molecular Biology, Vol. 8: Practical Molecular Virology: Viral Vectors for Gene Expression*, Ed. Collins, M. (Humana Press, Clifton, N.J.) 17–26 (1991). The indicator line (3T3-BAG) was prepared by transducing NIH 3T3 cells with the BAG virus, which contains both the β-galactosidase and the neo R genes. The 3T3 BAG cells (2×10$^5$) were cocultured with recipient mouse bone marrow cells (5×10$^6$), spleen cells, and superantants from the viral producer lines in 10 cm tissue culture dishes in the presence of 8 μg1m1 polybrene. When the cells reached confluence, the medium was removed and 4 ml of fresh medium was added to each dish. The supernatant was harvested after 16 hours, filtered through a 0.45 micron membrane filter, and stored at −80° C. until the assay was performed. The cycle of splitting and harvesting supernatant was repeated several times. Supernatants were analyzed for the presence of helper virus by infecting 3T3 cells with 2 ml/10 cm dish or 1 ml/6 cm dish for 2 hours at 37° C. in the presence of 8 μ/ml polybrene. Fresh medium was then added, and after 48 hours, the cells were harvested and assayed for lacZ expression by Xgal staining and for G418 resistance by replating 5×10$^5$ cells in the presence of G418 (400μ/ml). Control infections of 3T3 cells were performed with serial dilutions of BAG viral supernatants. These cells were positive for lacz expression and G418 resistance.

Supernatants from the psi-cre #4 and the PA-317 virus producing line (VPL) did not result in the generation of any blue cells in the BAG mobilization assay nor did any cells grow through G418 selection. Minced spleen and bone marrow from long term reconstituted mice were also studied by culture on BAG cells and compared to control tissues. In one of two controls, minced spleen co-culture resulted in one blue 3T3 cell in 2000 cells. The cells were further grown in G418 containing media. The supernatants from these G418 resistant cells were used to infect fresh 3T3 cell cultures. Again, 1 blue cell in 2000 cells was seen. No blue cells were seen in BAG cell controls. These results indicate the BAG mobilization assay detects low levels of a virus in control mouse tissues that is capable of rescuing the BAG-neo gene, but is unable to replicate or efficiently carry on cycles of infection. Similar results were seen in one of four spleen cocultures from long term reconstituted mice. These results demonstrate that the viral stocks and recipient animals are free of replication competent helper virus. Absence of a helper virus was confirmed in the PA-317 VPL by an independent laboratory (compliments of Dr. Frederick Schuening).

EXAMPLE 10

Enrichment of Human CD34+ Cells

Hematopoietic cells were applied to a Ficoll-hypaque gradient, and the light density cells were washed and resuspended at $1-2\times10^8$/ml in phosphate buffered saline (PBS) containing 1% bovine serum albumin (BSA). Biotinylated anti-human CD34+ monoclonal antibody (80ul per ml) was added and cells were incubated at room temperature for 25 minutes. The antibody-labeled cells were applied to the prepared avidin column, followed by a wash with PBS containing 1% BSA. The biotinylated anti-CD34+ antibody, the avidin column, and necessary reagents (CEPRATE LC (CD34+) Cell Separation System) are supplied by CellPro, Inc., Bothell, Wash. Adsorbed CD34+ cells were released by mechanical manipulation.

Figure 20A:
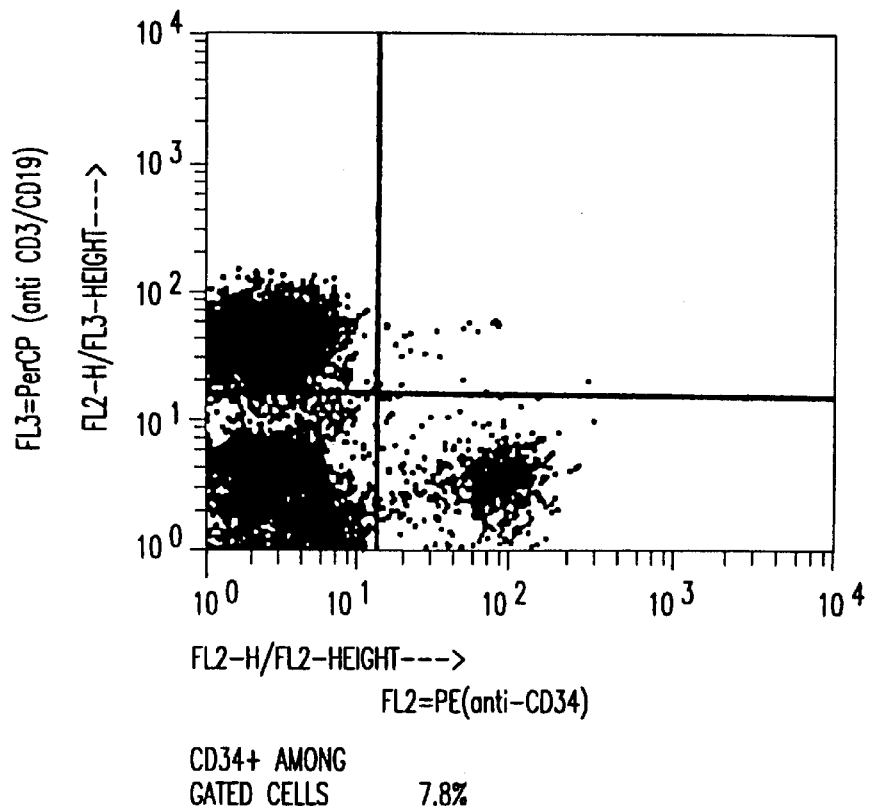
FIG. 20 (Parts A–B) Results of flow cytometry of hematopoeitic cells using anti-CD34+ monoclonal antibody to enrich for CD34+ cells (A). Post-enrichment analysis shows 87.6% CD34+ cells (B).
Figure 20B:
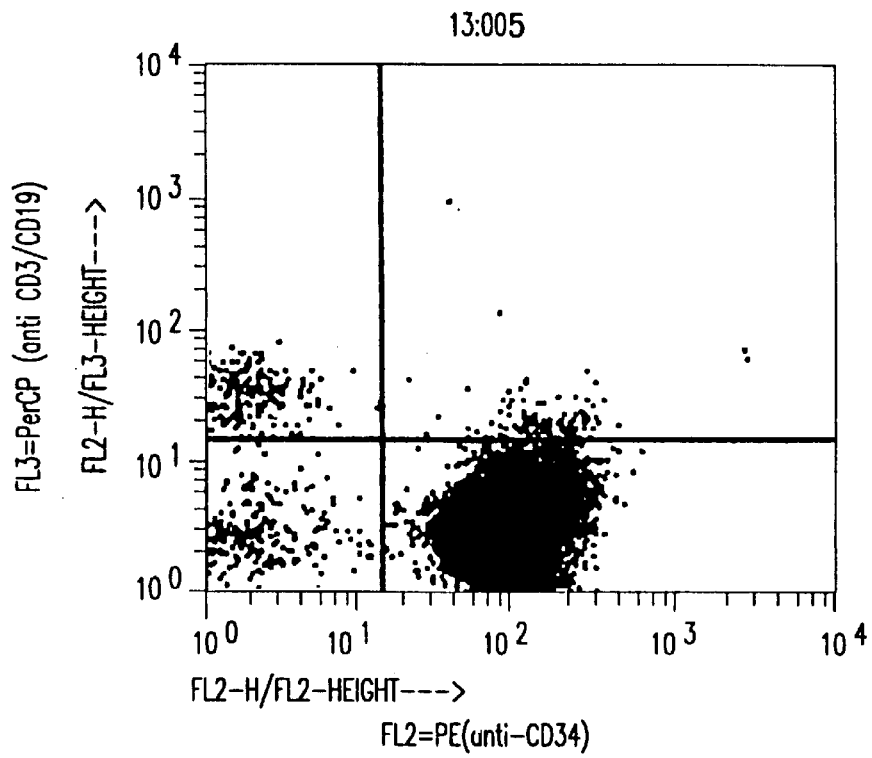
Figure 21:
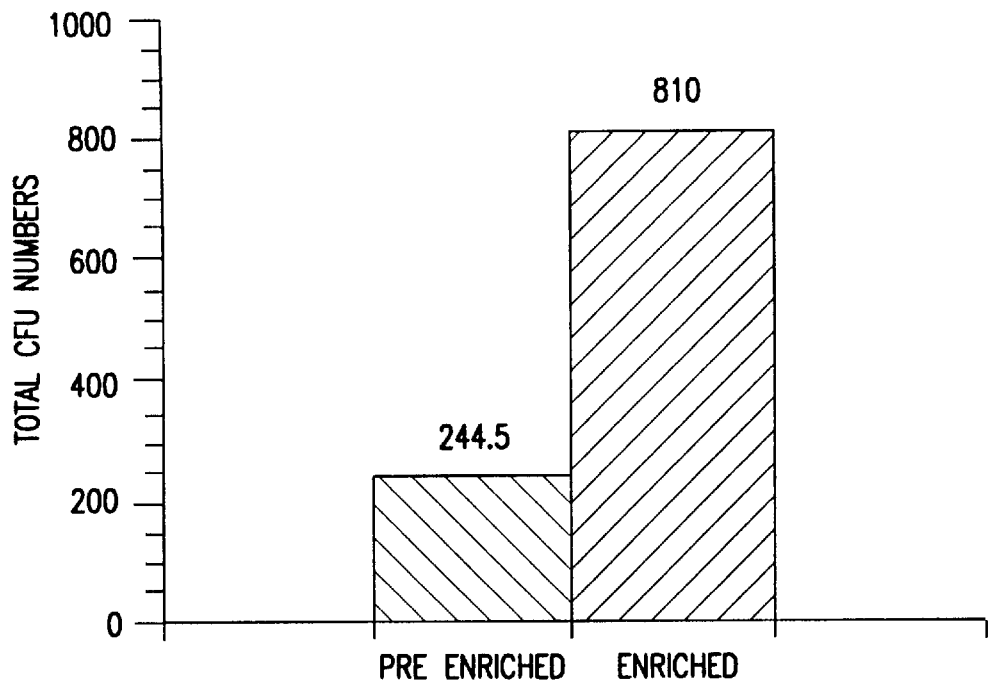
FIG. 21 Clonogenic assays of pre- and post-enriched samples to determine numbers of colony forming units (CFU) demonstrated increased numbers of CFU with CD34+ cells compared to the pre-enriched samples.

The results of a typical >10 fold enrichment, with 87.6% purity, are shown in FIG. 20. In these laboratory scale columns, enrichment is less than in the large clinical scale columns. Increased numbers of colony forming units (CFU) were consistently noted with CD34+ cells (B), compared to the pre-enriched samples (A). Clonogenic assays revealed an increase in CFU of about 3 fold (FIG. 21).

Prestimulation and Transduction of Human CD34+ Cells

Figure 22:
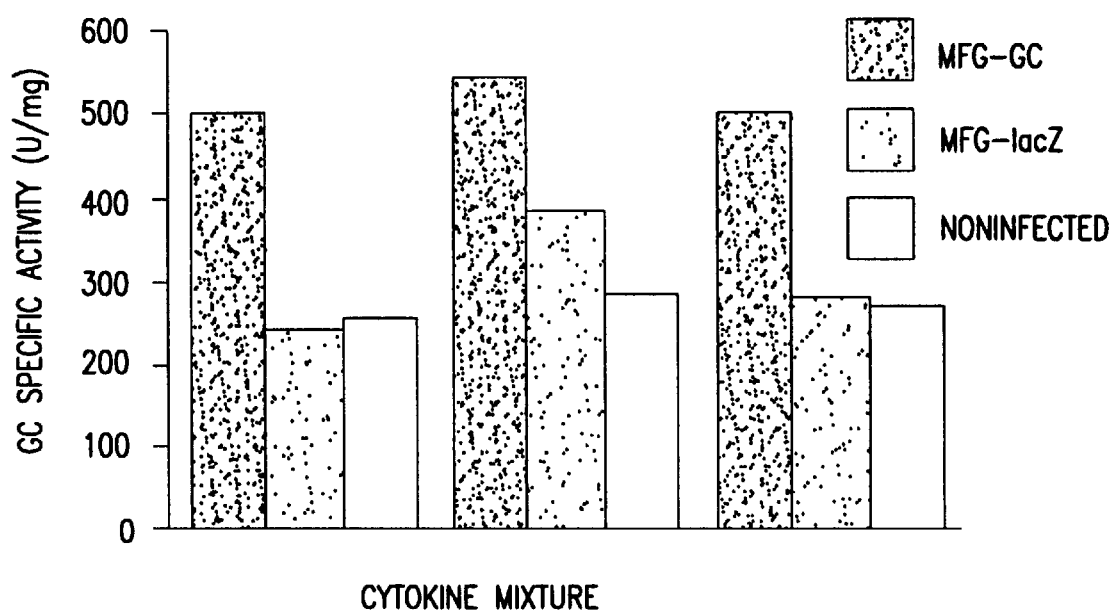
FIG. 22 CD34+ PB cells were exposed to viral supernatants 6 times over a period of 5 days beginning three days after incubation in mixtures of cytokines as indicated. Most of the cells were harvested one day after the final infection and were analyzed for enzyme activity. Values are the means for duplicate pellets.
Figure 23:
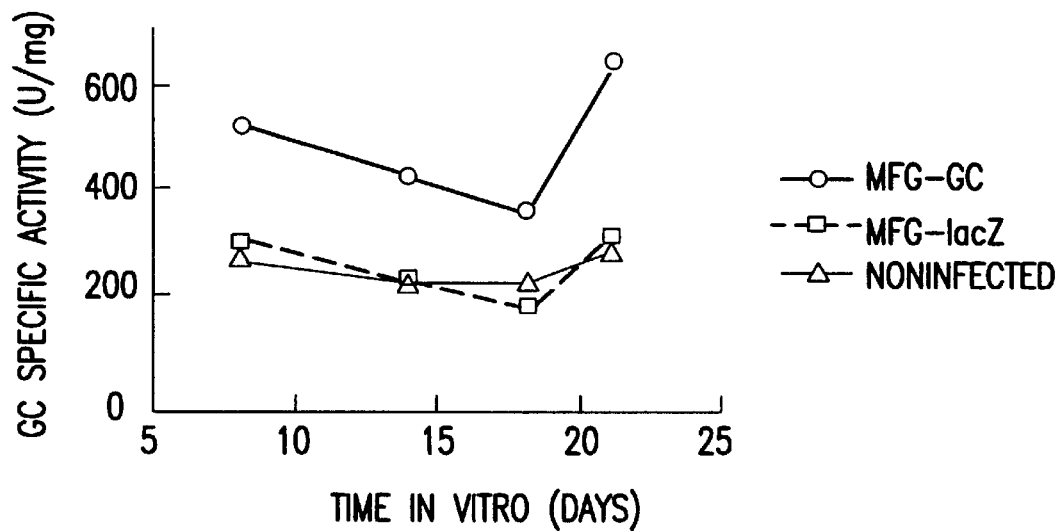
FIG. 23 Samples of infected and control CD34+ cells were harvested and analyzed for GC enzyme activity at the times indicated, while the remaining cells were further expanded in culture over a period of three weeks following infection.

Human long-term bone marrow culture medium (LTCM) was used for prestimulation and expansion of human CD34+ cells and for long term cultures. It consists of Iscove-Modified Dulbecco's Medium (IMDM) (Gibco BRL) containing 12.5% fetal bovine serum (FBS) (Hyclone Laboratories), 12.5% horse serum (HS) (Hyclone Laboratories), 2 mM L-glutamine, $1\times10^{-6}$M 2-mercaptoethanol, $1\times10^{-6}$M alpha-thioglycerol, 1 µg/ml hydrocortisone, and penicillin/streptomycin. CD34+ PB cells were exposed to viral supernatants 6 times over a period of 5 days, beginning three days after incubation, in mixtures of cytokines, as indicated. Most of the cells were harvested one day after the final infection and were analyzed for enzyme activity. Values given are the means for duplicate pellets. Results of experiments with human CD34+ enriched PB cells from G-CSF primed lymphoma patients show that transduction occurs and leads to expression of the glucocerebrosidase gene in these cells and their progeny using the MFG-GC retroviral vector. FIG. 22 shows enzyme activities of cells harvested shortly after infection in three different mixtures of cytokines: 1) IL-3, IL-6, SCF, and GM-CSF; 2) IL-3, IL-6, and SCF; and 3) SCF and PIXY. In each case, the enzyme activity in the MFG-GC infected group was more than 80% higher than the level of endogenous activity in noninfected cells grown under the same conditions. Control samples infected with a retroviral vector, containing the bacterial lacZ gene, did not differ significantly from noninfected cells, eliminating the possibility that increased activity from MFG-GC transduced cells was a result of nonspecific viral exposure or infection conditions. Samples of infected and control CD34+ cells were harvested and analyzed for GC enzyme activity at the times indicated, while the remaining cells were further expanded in culture over a period of three weeks following infection. Increased enzyme expression from the MFG-GC vector was evident immediately after infection, and this enhancement did not diminish with continued time in culture. Infected cells were expanded in vitro for three weeks following infection, and a sustained elevation was observed in enzyme activity in the experimental group versus control cells (FIG. 23). Southern blot hybridization of DNA from these cells suggested a transduction efficiency of 5 to 15%.

Figure 24:
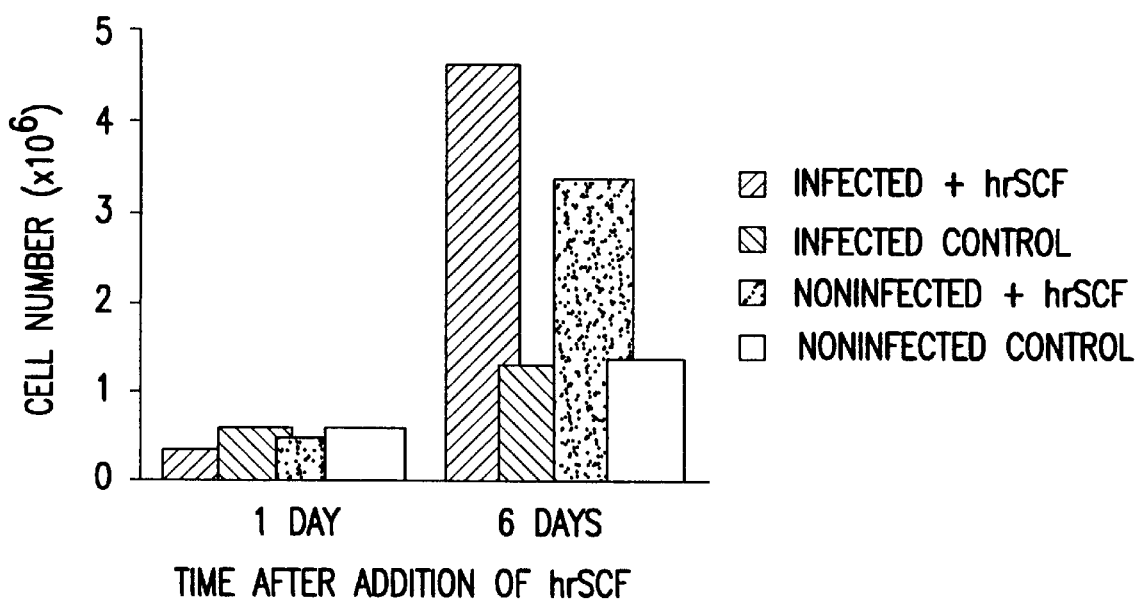
FIG. 24 Following infection and expansion into medium containing rrSCF, cell growth was observed to diminish. Aliquots of two samples were transferred to two dishes each, and to one dish from each sample was added hrSCF. These samples were incubated for an additional 6 days prior to counting cell numbers in a hemacytometer.

In two subsequent experiments (Experiments #2 and #3), significantly increased GC expression was not observed following infection procedures. In these experiments, rat recombinant SCF (rSCF) was used during infection and expansion of the cells. Although the biological activity of this factor was expected to be similar to that of human recombinant SCF (hrSCF) (Langley, K. E., et al., Arch. Biochem. Biophys. 295(1):21–28, 1992), it became clear in Experiment #4 that the cytokine activity was suboptimal using rSCF from this particular source. Following infection and expansion into medium containing rrSCF, cell growth was observed to diminish. Aliquots of two samples were transferred to two dishes each, and to one dish from each sample was added hrSCF. These samples were incubated for an additional 6 days prior to counting cell numbers in a hemacytometer (FIG. 24).

Figure 25:
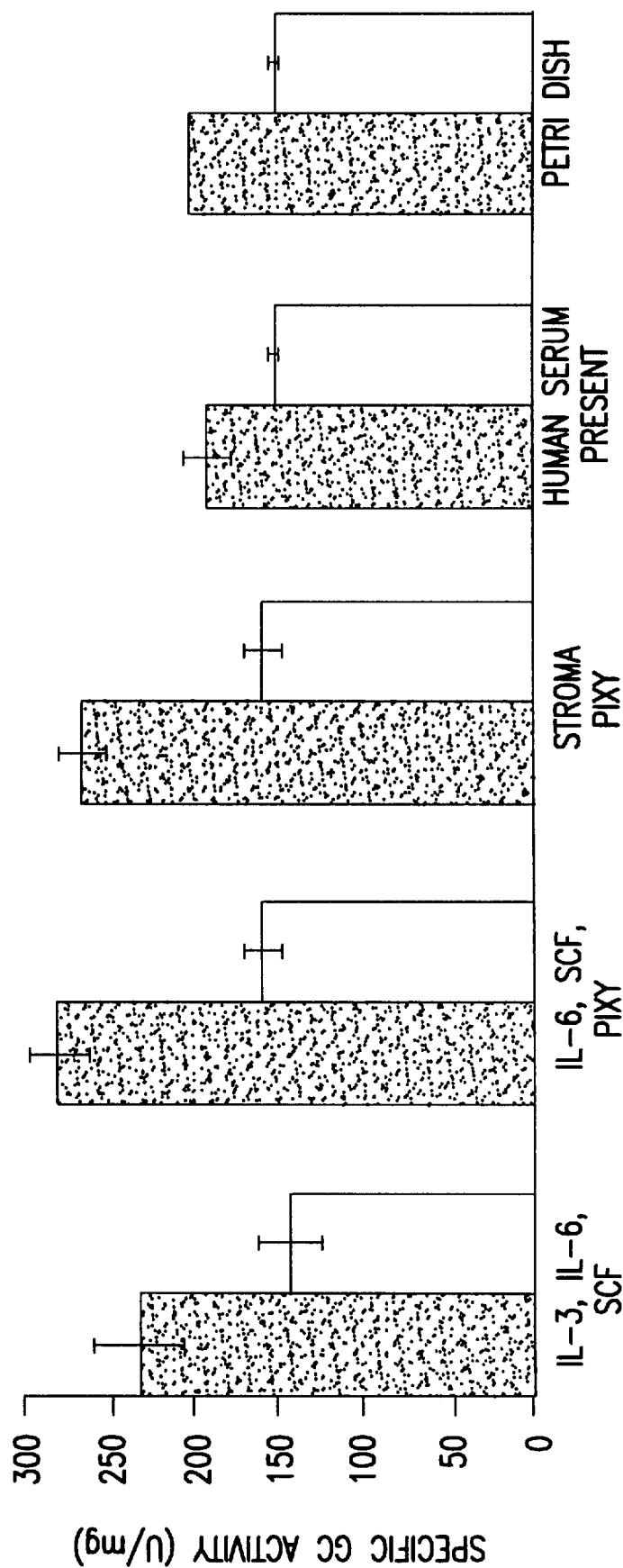
FIG. 25 CD34+ PB cells were infected and expanded under different conditions as described in the test. One day after the final infection, cells were harvested and were analyzed for GC specific activity. Error bars indicate mean +/−se (n=3).

In the next experiment (#4), cells were harvested at the point at which a decline in growth rate was observed. Analysis of glucocerebrosidase activity in these cells indicated that elevation of activity had occurred in each of several different groups following infection, in comparison to similarly cultured noninfected cells. These cells had been infected under a variety of conditions in an effort to uncover a reason for the lack of response in the two previous experiments. Two mixtures of cytokines were used: 1) IL-3, IL-6 and SCF, or 2) PIXY, IL-6 and SCF. The latter group was further subdivided into cells infected in the presence of a stromal cell layer, in the presence of human serum, on Petri dishes and on treated tissue culture dishes. The specific activity of these samples was lower across all the groups than in previous experiments (control cells ~150 U/mg vs >200 U/mg), perhaps as a result of the declining viability of these cells at the time, but the elevation for infected cells was about 70% above endogenous levels (FIG. 25).

Figure 26:
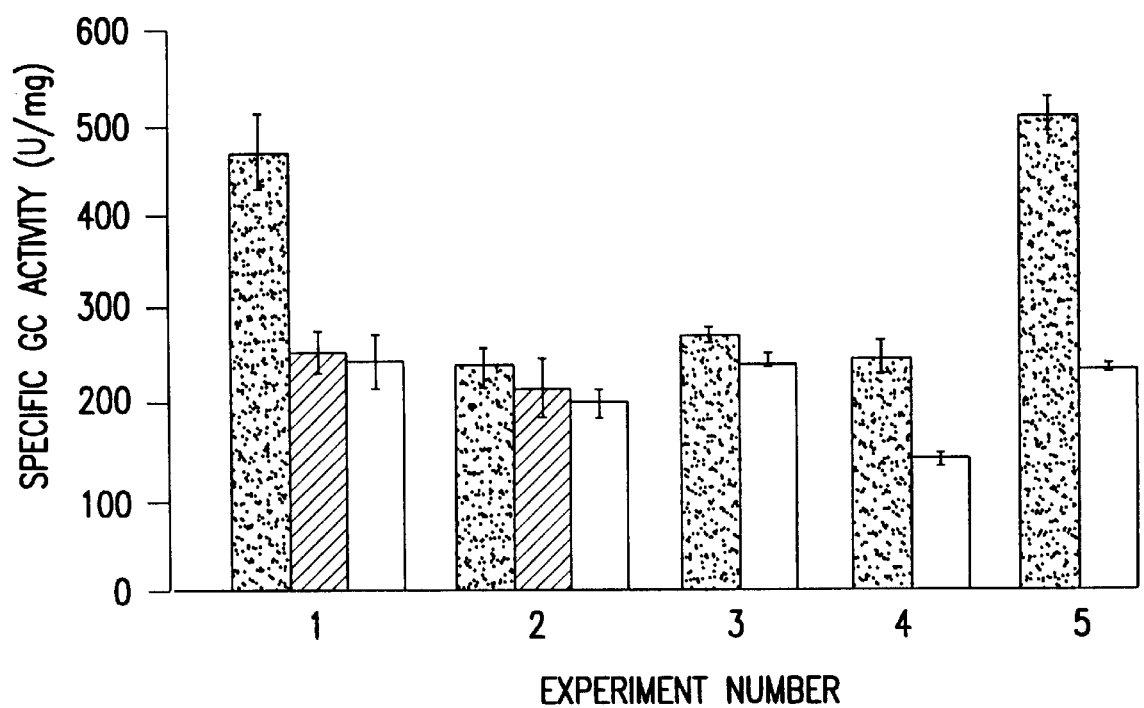
FIG. 26 Summary of experiments 1–5, showing enzyme activity in CD34+ PB cells following infection with MFG-GC containing supernatants. See text for details. Error bars indicate mean +/−se (n=4 or more cell pellets analyzed, except Experiment 5; control n=2).

In Experiment #5, for which recombinant human SCF was used throughout infection and expansion phases, the specific activity was once again >200 U/mg, an increase of more than 100% above endogenous GC activity. FIG. 26 provides a summary of experiments 1–5 showing GC enzyme activity in human CD34+ PB cells following infection with MFG-GC containing supernatants.

Figure 27:
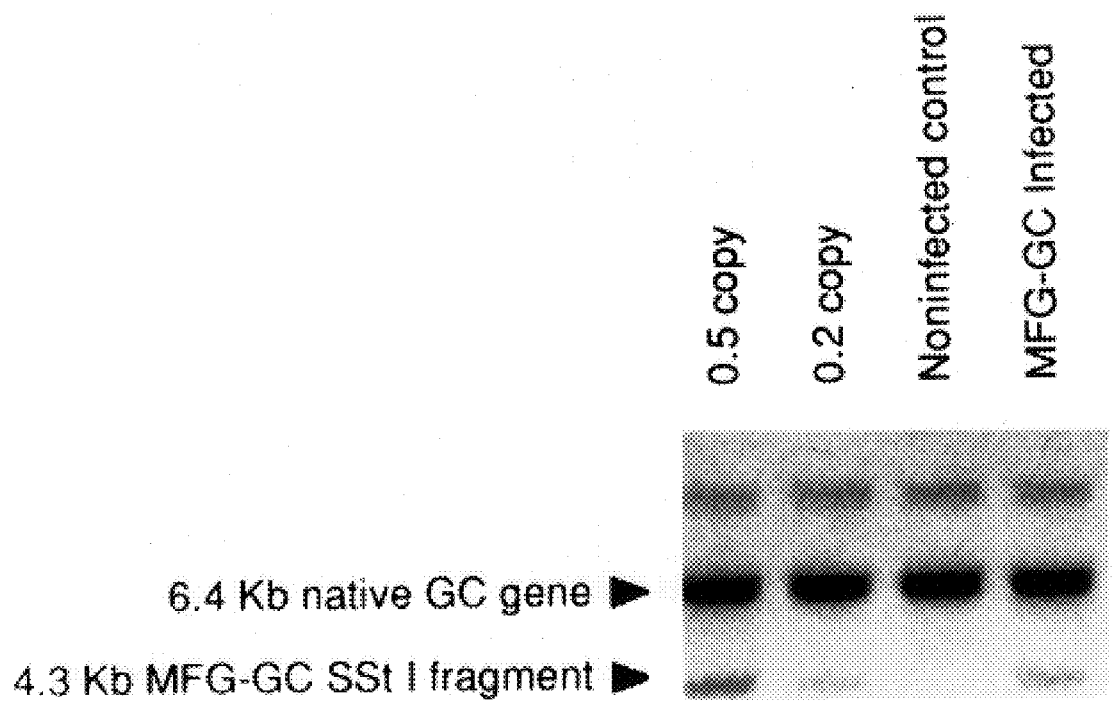
FIG. 27 Southern blot hybridization of Sst 1 digests of DNA from infected and noninfected CD34+ enriched PB cells (Experiment 5). The 4.3 kb fragment (apparent mol. wt.) in the vector, to which the 1.8 kb GC cDNA probe hybridizes, as well as the 6.4 kb Sst 1 fragment of the normal GC gene and the pseudogene are shown. Copy number controls are shown, prepared from known amounts of DNA from a murine cell line containing 5 copies per cell.

Southern blot hybridization of Sst 1 digests of DNA from infected and noninfected CD34+ enriched PB cells was performed (Experiment 5). Copy number controls were prepared using known amounts of DNA from a murine monoclonal cell line containing 5 copies per cell. Sst 1 cuts within the LTRs on each end of the vector to release the 4.3 kb fragment (apparent mol. wt.), to which the 1.8 kb GC cDNA probe hybridizes. In human cells the probe also binds strongly to the 6.4 kb Sst 1 fragment of the normal GC gene and the pseudogene. Southern blot hybridization suggested a transduction efficiency of >20% (FIG. 27).

Figure 28:
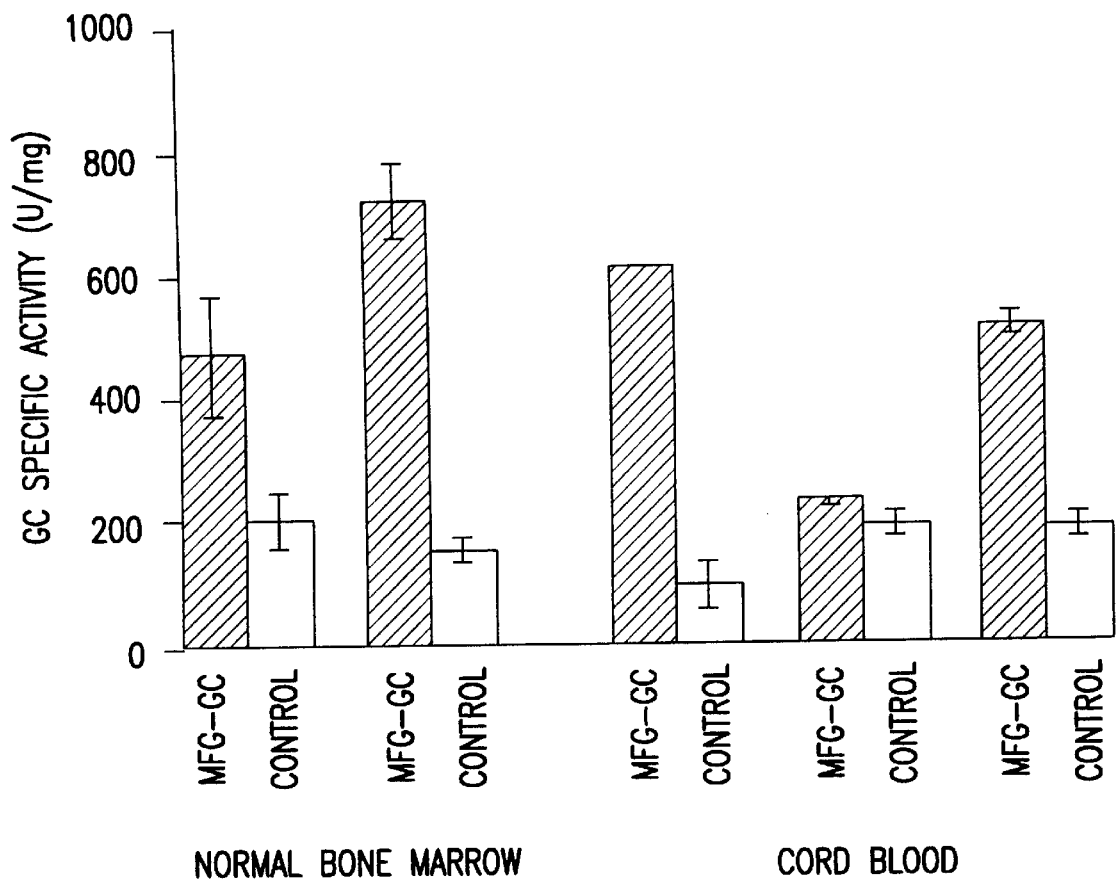
FIG. 28 GC activity from CD34+ cells isolated from normal bone marrow and cord blood transduced with MFG-GC relative to control (noninfected) cells.

FIG. 28 shows the results of subsequent experiments, which demonstrate that normal CD34+ cells are transduced and express 2–4 times the normal activity of GC. Some of the variables that affect the transduction efficiency and resultant expression of GC in human CD34+ cells have also been explored. It is believed that the combination of IL-3, IL-6 and SCF (each at 10 ng/ml) provides the most consistent results for GC expression.

Figure 29:
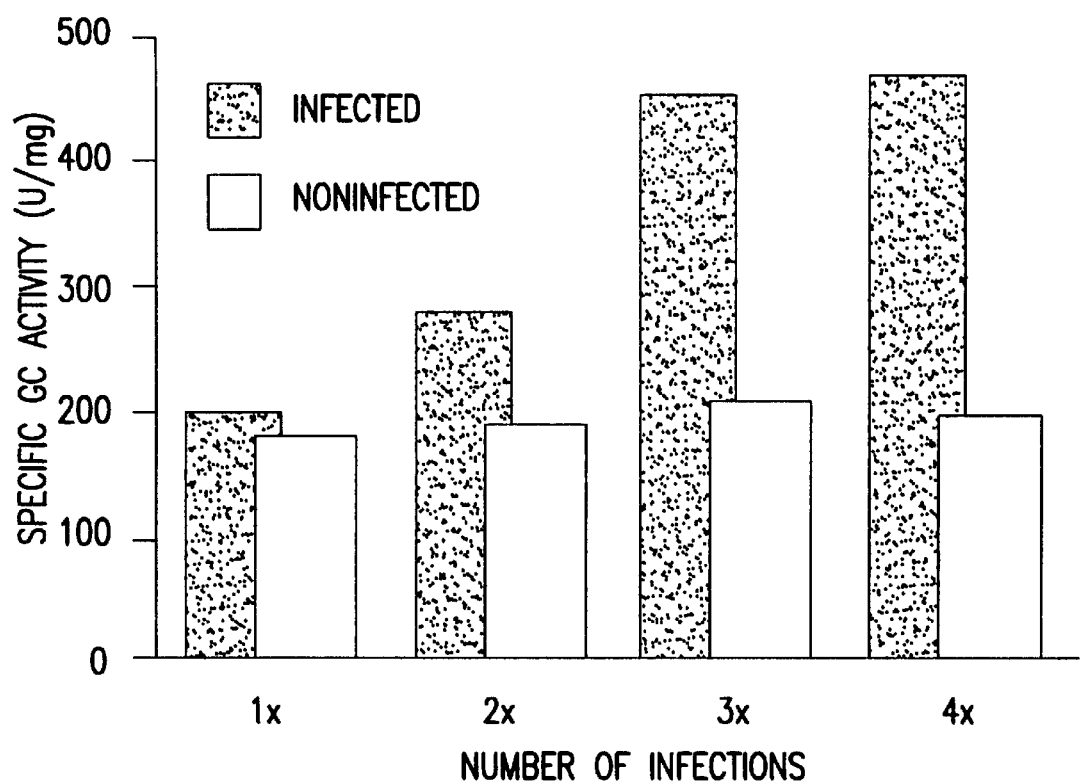
FIG. 29 Human bone marrow CD34+ cells were infected by daily exposure to virus-containing supernatant for 4 days. Prior to the second and each subsequent infection, an aliquot of cells was transferred to a separate dish without further exposure to virus. After the infection period, cells were expanded and harvested for analysis of enzyme expression.

Human bone marrow CD34+ cells were infected by daily exposure to virus-containing supernatant for 4 days. Prior to the second and each subsequent infection, an aliquot of cells was transferred to a separate dish without further exposure to virus. After the infection period, cells were expanded and harvested for-analysis of enzyme expression. There is a linear relationship between total number of doses of viral supernatants and GC activity expressed in CD34+ cells (FIG. 29).

Figure 30:
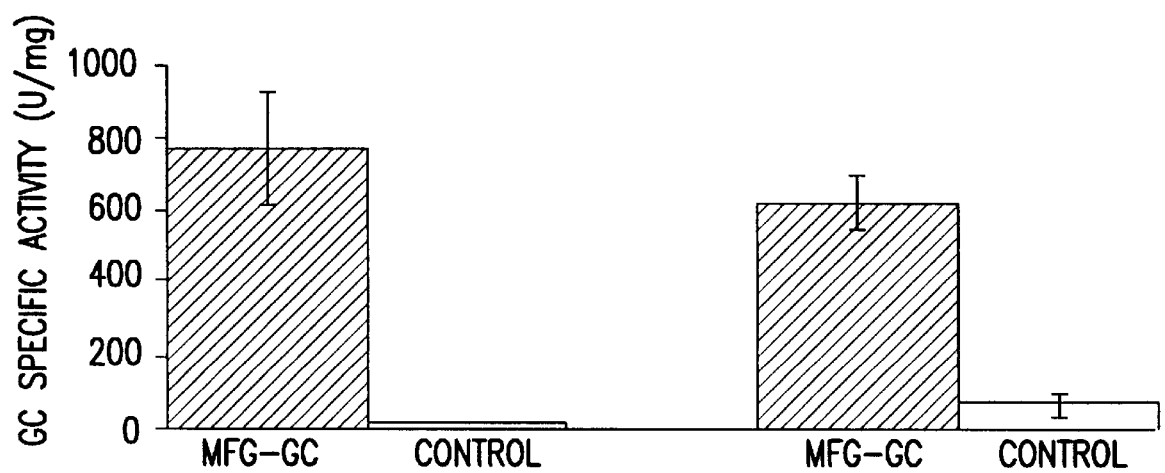
FIG. 30 GC activity of MFG-GC transduced CD34+ cells from Gaucher bone marrow relative to noninfected control cells.

Using the conditions described above, CD34+ cells obtained from the bone marrow of Gaucher patients have shown an increase in GC activity of 20–40 fold, essentially equaling the results in transduced CD34+ cells from controls (FIG. 30). These cells kept in culture for 3 weeks maintain the elevated levels of glucocerebrosidase activity.

Figure 31A:
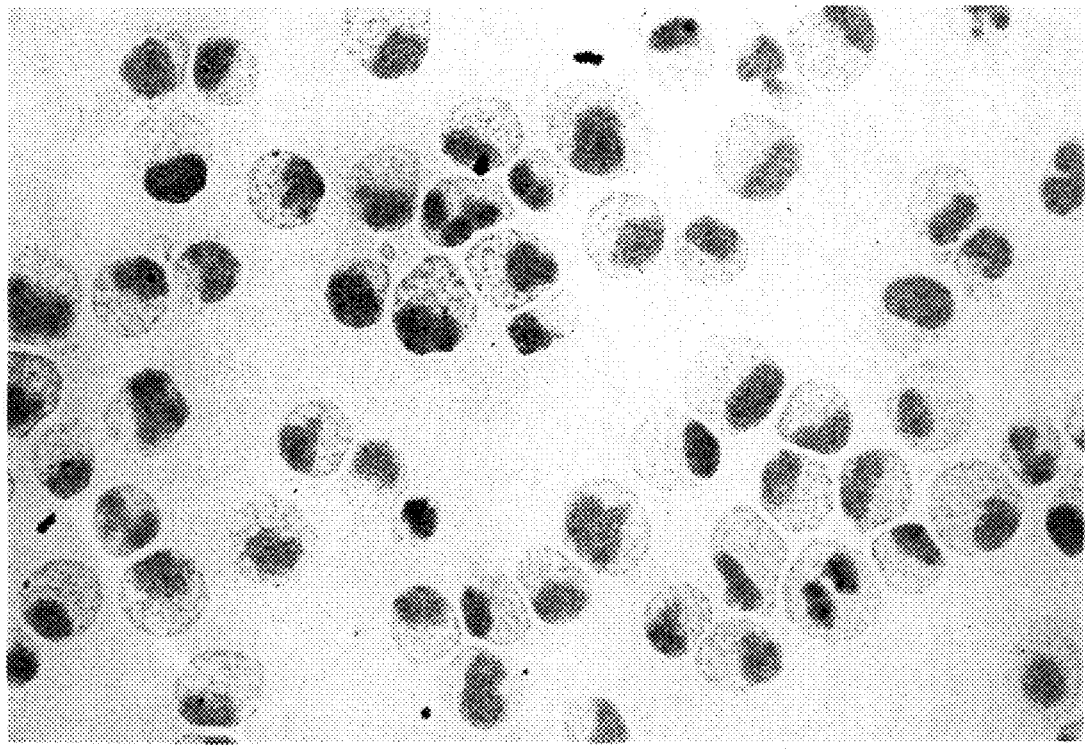
FIG. 31 (Parts A–B) Immunocytochemical staining for human glucocerebrosidase (GC). Cytospin preparations were stained using the monoclonal antibody 8E4. Normal human GC stains red in Gaucher marrow transduced with the MFG-GC vector (A), while no staining occurred in nontransduced Gaucher marrow cells (B).
Figure 31B:
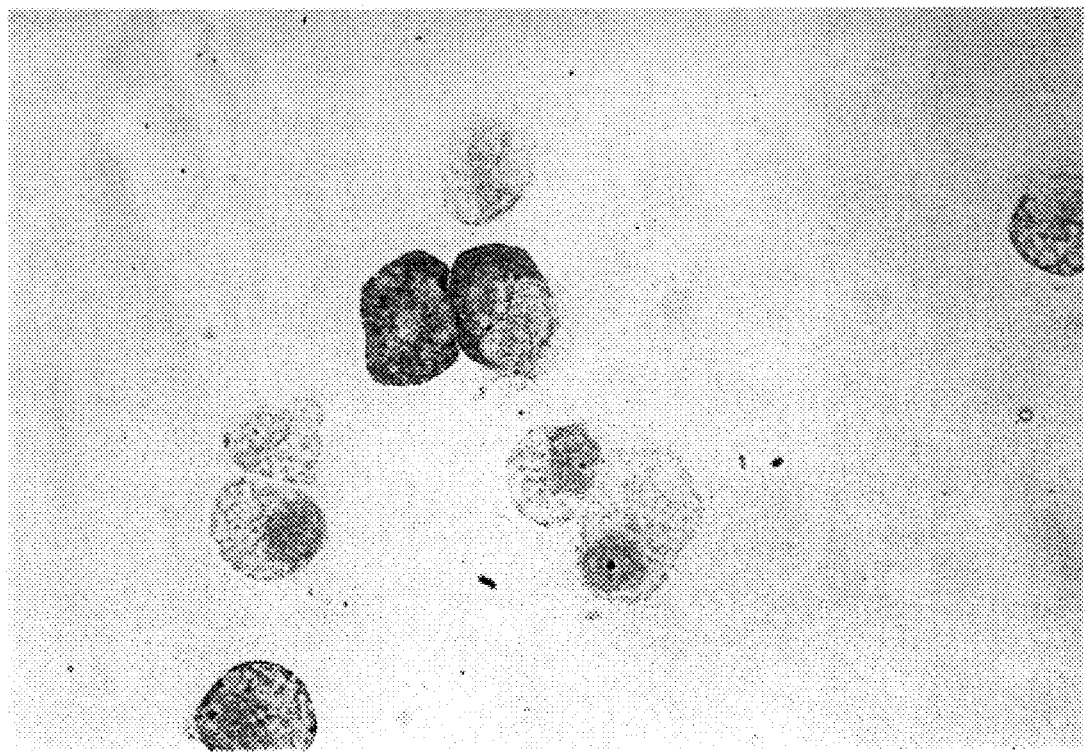

Gaucher CD34+ cells were rapidly evaluated for transduction efficiency using a conventional chromogenic immunocytochemical assay for glucocerebrosidase. Immunocytochemical staining for human glucocerebrosidase (GC) utilized cytospin preparations stained with the monoclonal antibody 8E4. Using this procedure, as shown in FIG. 31, CD34+ cells from a Gaucher patient gave no detectable color formation (B), whereas, many cells in the infected population gave a strong signal (see FIG. 31). Counting ten high power fields and scoring for immunocytochemical positive cells, an estimated transduction efficiency of approximately 20% was calculated.

The colony forming efficiency in methylcellulose was determined for freshly enriched CD34+ cells and for infected and control cells following infection procedures. Results from many experiments indicated that between 30–100% of the colony forming efficiency remains after infection.

Optimal Conditions for Transduction of Human CD34+ Cells

Procedures for the optimal transduction of CD34+ cells have been determined (Bahnson, A. B., et al., *Gene Therapy* 1(3):176–184, 1994; Bregni, M., et al., *Blood* 80:1418–1422, 1992; Langley, K. E., et al., *Arch. Biochem. Biophys.* 295 (1):21–28, 1992). Centrifugation of target cells with viral supernatant was examined. Initially, the results of this procedure was measured in a cell line (TF-1) and in 3T3 cell targets. These studies demonstrated activities of GC in excess of 10 fold above the baseline in these targets. The parameters of optimal speed of centrifugation, length of centrifugation, shape of vessel, number of procedures, and temperature at which the procedure is performed was examined. The conclusions from these experiments were that a speed of 10,000×g in a round bottom tube repeated 2–3 times over several days, was optimal. The length of time in the centrifuge increased the resultant GC activity in the targets and was linear out to 400 minutes. Room temperature or 37° C. did not make a significant difference. Centrifugation was then applied to CD34+ cells to examine its value on the transduction of these cells for use in clinical gene therapy protocols for Gaucher patients.

A protocol was used in which $5 \times 10^5$ CD34+ cells were centrifuged at 2400×g for 2 hours with either 0.2 ml or 1.0 ml of viral containing supernatant with a titer of $5 \times 10^6$ pfu/ml. The results of these studies showed that three infections were optimal and yielded enzymatic GC activity of 10–15 times that of uninfected CD34+ cells. PCR analysis of CFU-GM derived from these cells revealed a transduction efficiency of 100%. The GC activity of CD34+ cells expanded for 17 days in culture remained at levels >5 times the control, uninfected cells.

EXAMPLE 11
Construction of R-GC Vector

The R-GC retroviral vector was developed from the MFG-GC vector, by the insertion of a Sac II linker placing the gag sequences out of frame thus rendering the vector unable to synthesize truncated gag-related peptides. It also provided another site of sequence dissimilarity making recombination events to wild type less of a possibility. After partial Sma I digestion of the vector, this additional safety step was accomplished by inserting an eight base pair Sac II linker 3' to Hae III site at the ATG of the half-gag gene in the retroviral sequence.

Figure 32:
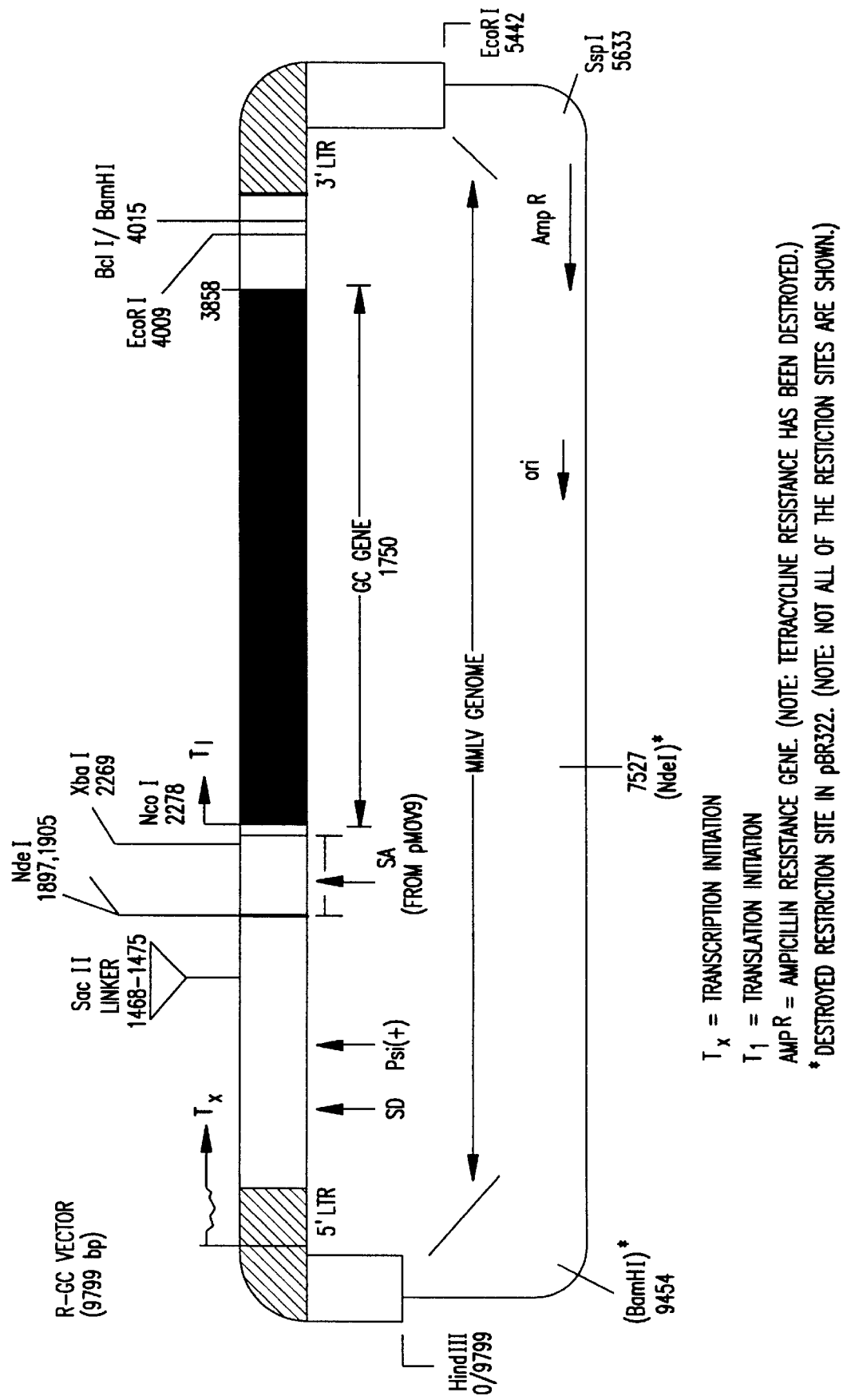
FIG. 32 Structure of R-GC retroviral vector.

The retroviral vector, R-GC, containing the gene for glucocerebrosidase (GC) is a replication defective vector. The structure of R-GC is shown in FIG. 32.

Generation of the YCRIP GC Producer

The viral producer line of R-GC was developed by infection of the psi crip packaging line (Danos, O., et al., *Proc. Natl. Acad. Sci. USA* 85:6460–6464, 1988) by supernatant from BOSC cells (Pear, W. S., et al., *Proc. Natl. Acad. Sci. USA* 90:8392–8396, 1993) transfected by the R-GC plasmid. Selection of high titer producer cells was done by GC enzymatic assay screening and confirmed by Southern blot analysis. The producer is free of bacteria, mycoplasm, and replication competent retrovirus.

Figure 33:
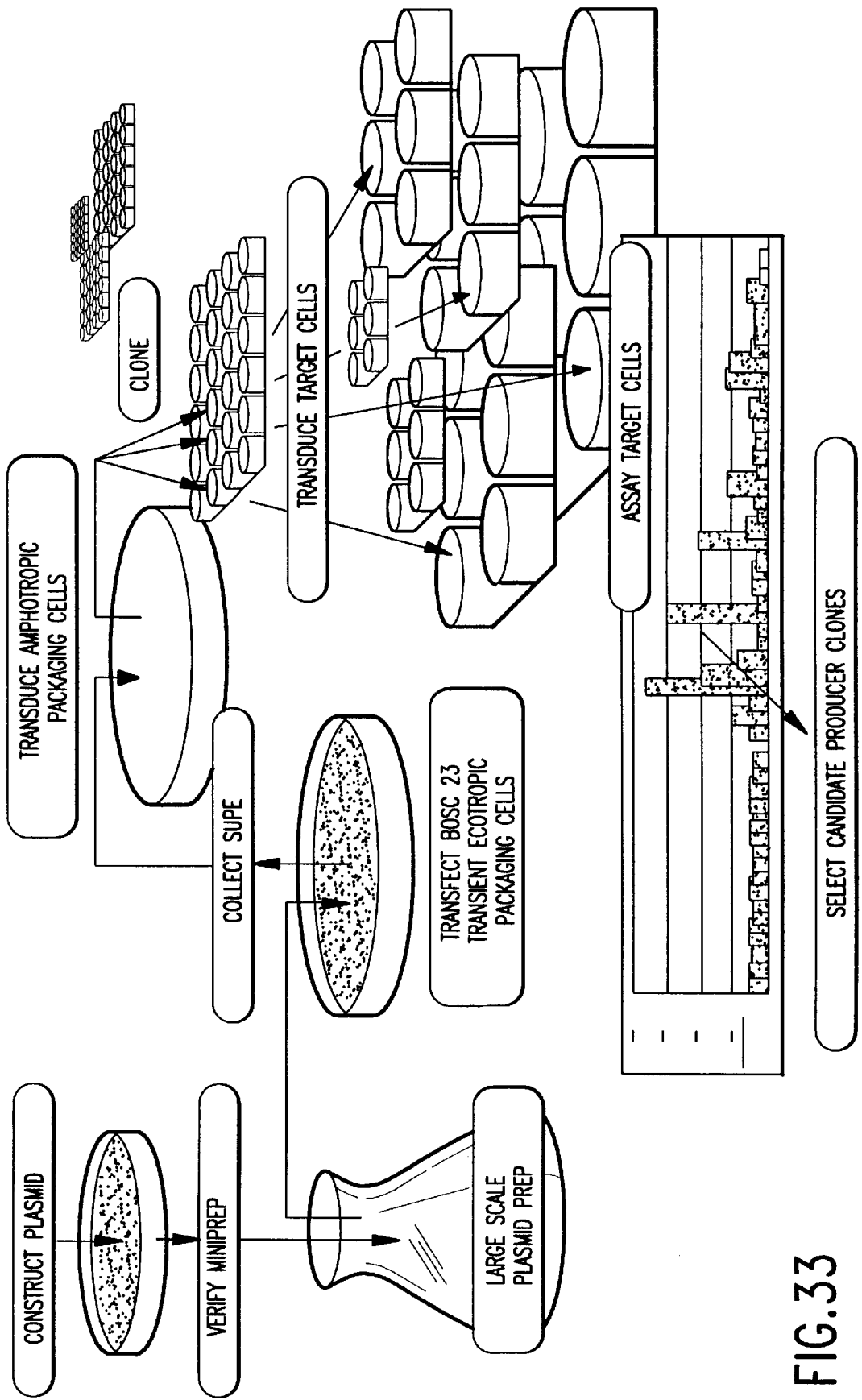
FIG. 33 Diagrammatic representation of cross-infection strategy for deriving R-GC producer cell clones.

The producer line was obtained using a two step procedure (FIG. 33). First, the plasmid form of the vector was transiently transfected using calcium phosphate/DNA precipitation into BOSC 23 cells (Pear, W. S., et al., *Proc. Natl. Acad. Sci. USA* 90:8392–8396, 1993), from which were obtained ecotropic vector-containing supernatants. Secondly, these supernatants were used to cross-infect amphotropic YCRIP packaging cells. High GC enzyme levels (~10× control) in the infected YCRIP cells indicated that the BOSC 23 cells had efficiently packaged the R-GC vector. Clones were obtained from the infected YCRIP cells using limiting dilution without selection. Supernatants from these clones were screened by infection of 3T3 targets (FIG. 33), and the highest titer clones were selected for further characterization.

Gene Transfer and Expression in 3T3 Target Cells Using the R-GC Vector

Figure 34:
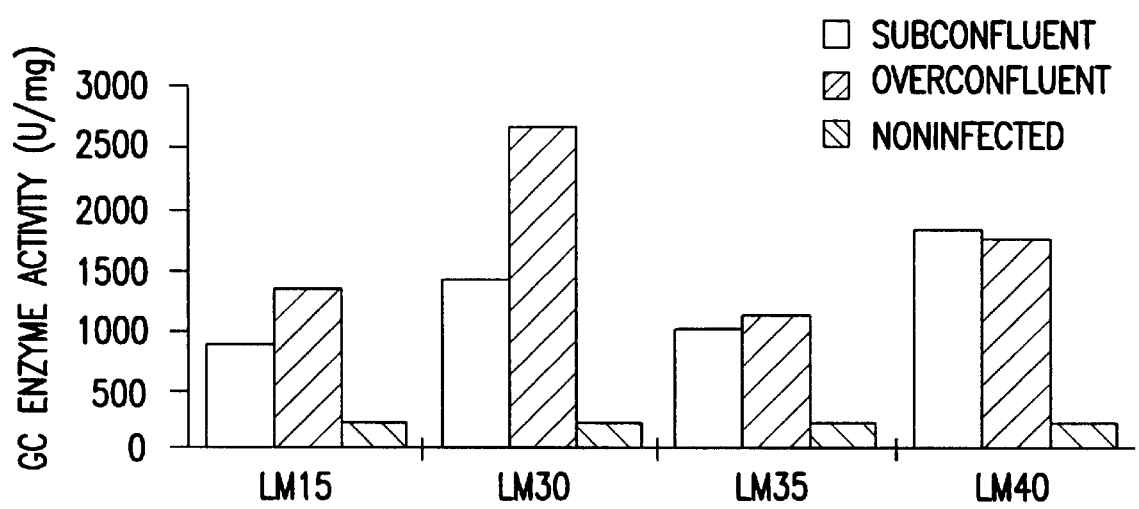
FIG. 34 R-GC supernatants assayed on 3T3 target cells for GC activity to select the highest titer amphotropic producer (LM30).

Following the initial screening, the cells were expanded into monolayers for comparison of the highest titer clones under similar conditions of confluence. With the amphotropic producer of MFG-GC (cc-2), maximal titers are obtained with fully confluent and/or "overconfluent" monolayers (Bahnson, A. D., et al., *Gene Therapy*, 1(3):176–184, 1994), and similar results have been obtained for the highest titer amphotropic producer of R-GC (LM30) (FIG. 34). The four highest titer clones were compared under conditions of subconfluence and "overconfluence" for production of vector-containing supernatants. Supernatants were assayed on 3T3 targets using standard procedures.

Based on the above and additional data, clone LM30 was chosen for expansion and further characterization. To test the stability of these cells, cryogenically preserved LM30 cells, were thawed and re-expanded to confluent monolayers, from which supernatants have been tested and compared with previously prepared supernatant.

Figure 35:
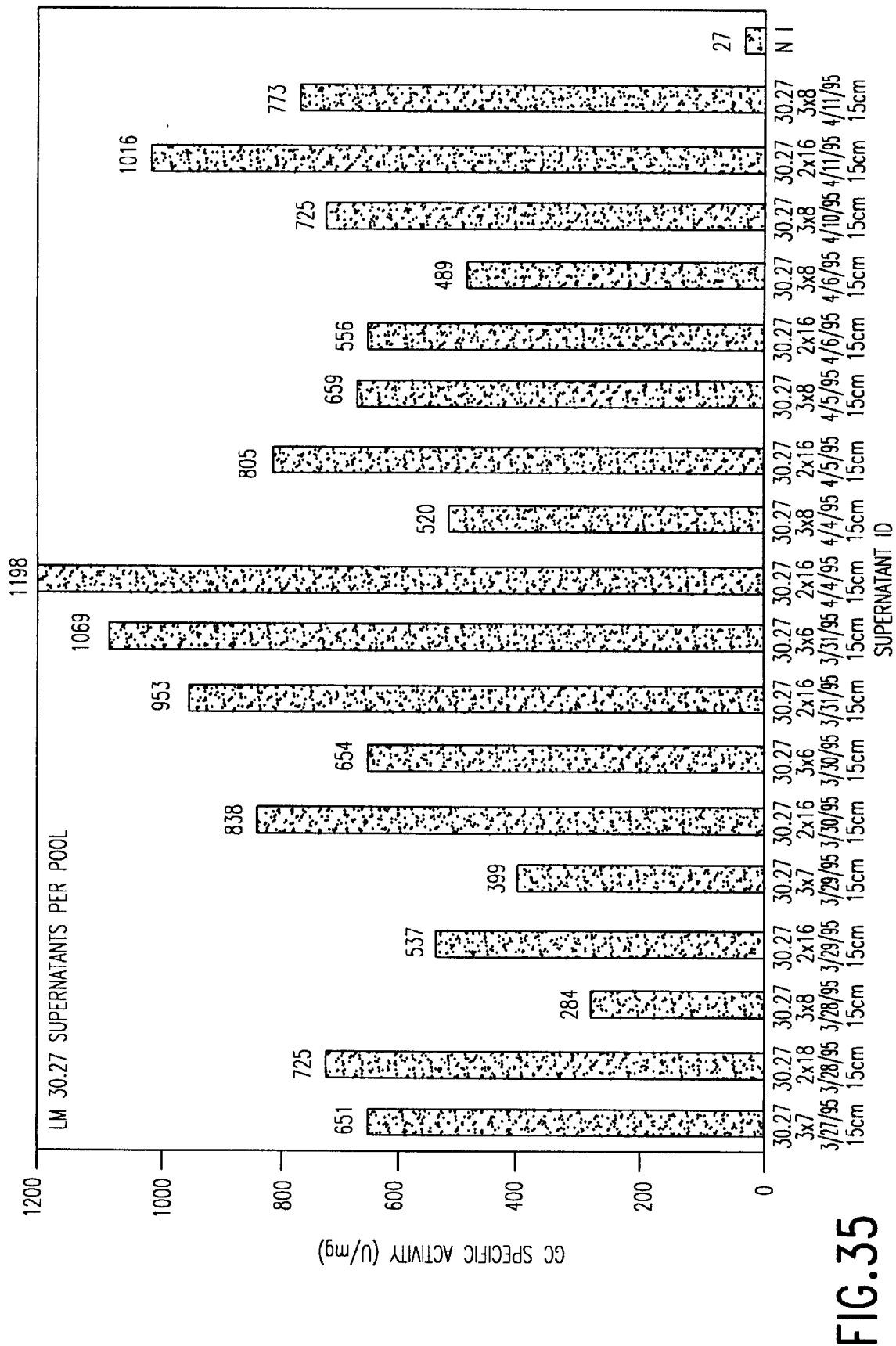
FIG. 35 The GC activity conferred on target cells infected by LM30 supernatants collected periodically over a continuous period. The relative titer of the LM30 producer was maintained over time for as long as 2 years.

The ability of the LM30 clones to generate a titer that is approximately equal to the original titer was tested over a period of two years. The original clone was produced in 8/92. Frozen vials prepared in 6/93 were thawed in early 1995 and supernatants generated from the producer over several weeks. These supernatants were able to impart enzymatic activity on target cells that was equal to or greater than the activity conferred on the target cell line more than two years earlier (FIG. 35).

These cells have been used to generate supernatant for use in a variety of tests, including the verification of equivalence of the R-GC vector to the MFG-GC vector, the ability to infect and yield GC expression in human CD34+ cells, demonstration of stability of the producer and of the vector-containing supernatants over time, and additional investigations into possibilities for concentration of virus and optimization of conditions for efficient transduction.

EXAMPLE 12
R-GC Gene Transfer and Expression in Human CD34+ Cells From Blood

Figure 36:
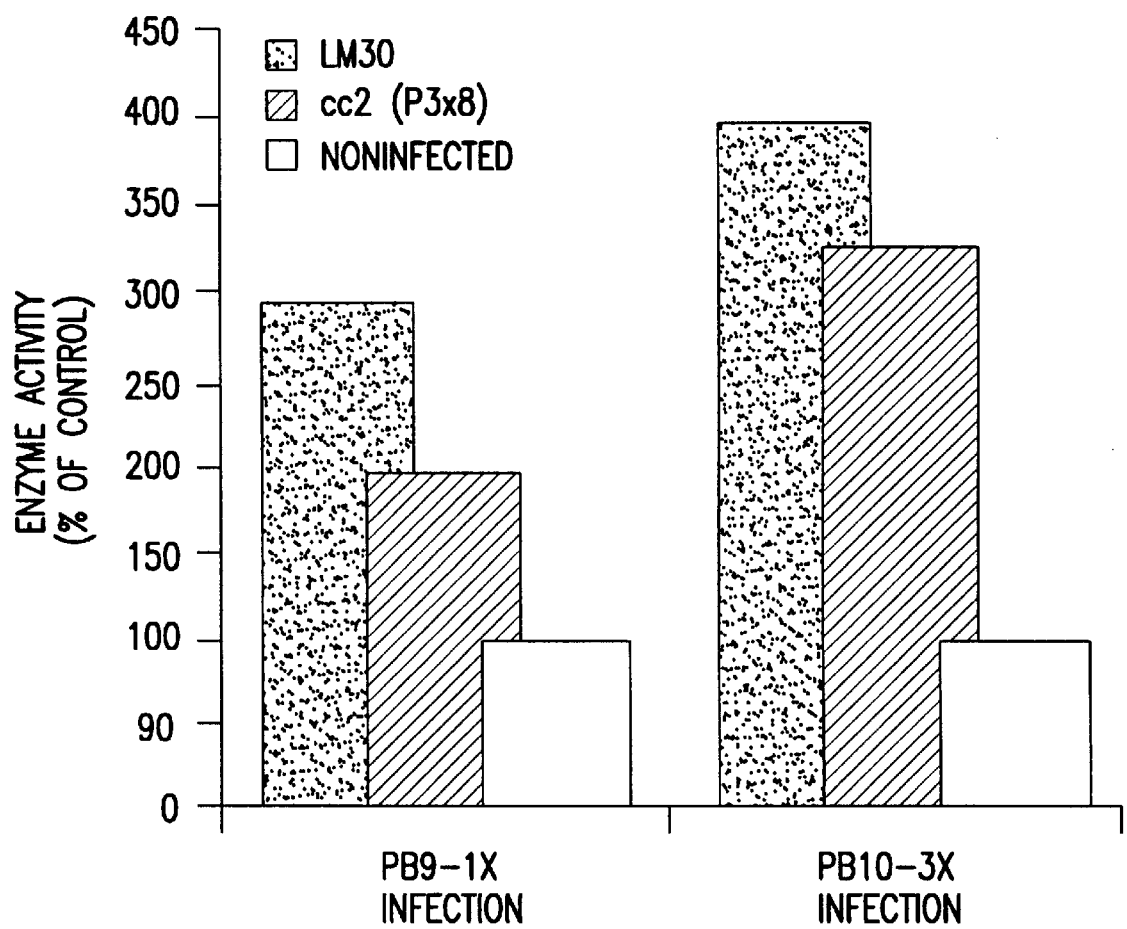
FIG. 36 R-GC and MFG-GC were obtained from the YCRIP producer cell lines, LM30 and cc-2, respectively. The cc-2 supernatant was from the highest-titer pooled batch, P3×8—Aug. 24, 1993. The LM30 supes were from the highest-titer individual supernatants available at the time: PB9=LM30 3×6—Dec. 20, 1993, and PB10=LM30b 3×9—Feb. 7, 1994. The cells from PB9 were 5% CD34+ by FACS analysis, and were infected with only one addition of supernatant. The cells from PB10 were more highly enriched for CD34+ (~40%), and were infected with three exposures to fresh supernatant over 1.5 days. Both protocols included a 24 hour prestimulation in medium containing IL-3, IL-6, and SCF. Results for enzyme activity are expressed relative to mock-infected control cells exposed to 10%CS/DMEM and cultured in an identical manner to the infected cells in each experiment. Noninfected control activities were 165 and 44 U/mg for PB9 and PB10, respectively.

The GC enzyme activity of R-GC infected CD34+ cells from the peripheral blood of two Gaucher patients was more than two fold above control noninfected cells after 1× infection and about four fold above controls after 3× infections with supernatant from the LM30 clone (FIG. 36). In these experiments, supernatants from the cc-2 clone (producer of nonmodified MFG-GC) were also tested for comparison. R-GC and MFG-GC were obtained from the YCRIP producer cell lines, LM30 and cc-2, respectively. The cc-2 supernatant was from the highest-titer pooled batch, P3×8—Aug. 24, 1993. The LM30 supes were from the highest-titer individual supernatants available at the time: PB9=LM30 3×6—Dec. 20, 1993, and PB10=LM30b 3×9—Jan. 7, 1994. The cells from PB9 were 5% CD34+ by FACS analysis, and were infected with only one addition of supernatant. The cells from PB10 were more highly enriched for human CD34+ (~40%), and were infected with three exposures to fresh supernatant over 1.5 days. Both protocols included a 24 hour prestimulation in medium containing IL-3, IL-6, and SCF. Results for enzyme activity are expressed relative to mock-infected control cells exposed to 10%CS/DMEM and cultured in an identical manner to the infected cells in each experiment. Noninfected control activities were 165 and 44 U/mg for PB9 and PB10, respectively.

Figure 37:
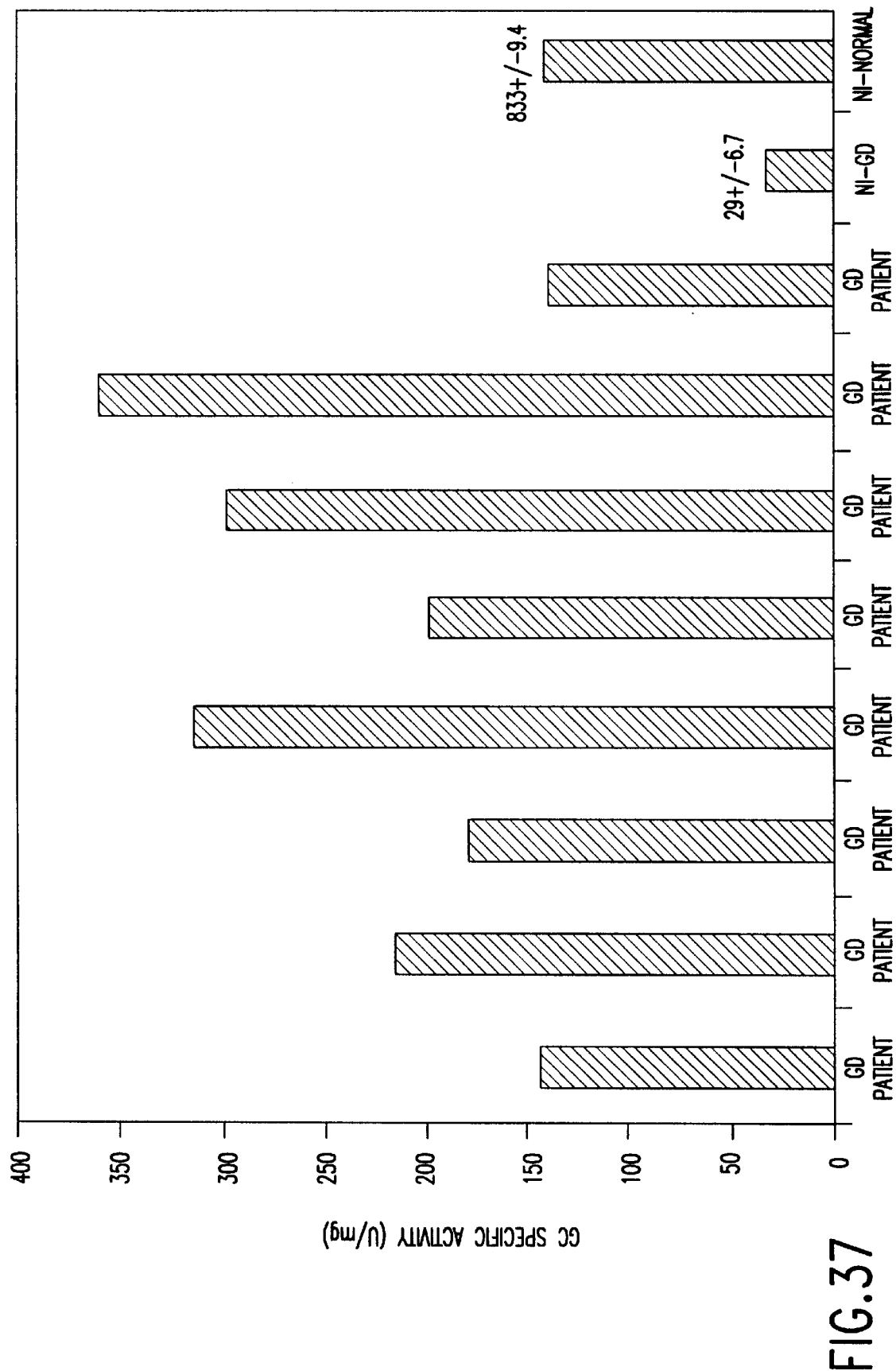
FIG. 37 The GC activity in 8 separate samples of R-GC transduced CD34+ cells from 2 Gaucher patients, in which all evidenced the restoration of GC activity to at least that of normal cells. NI=noninfected. GD=Gaucher disease.

The R-GC vector was used to infect 8 separate samples of CD34+ cells obtained from two patients. Infection was carried out in sterile 150 ml plasma transport bags using a single centrifugation promoted infection protocol. GC activity was restored to at least normal in each experiment (FIG. 37).

Figure 38:
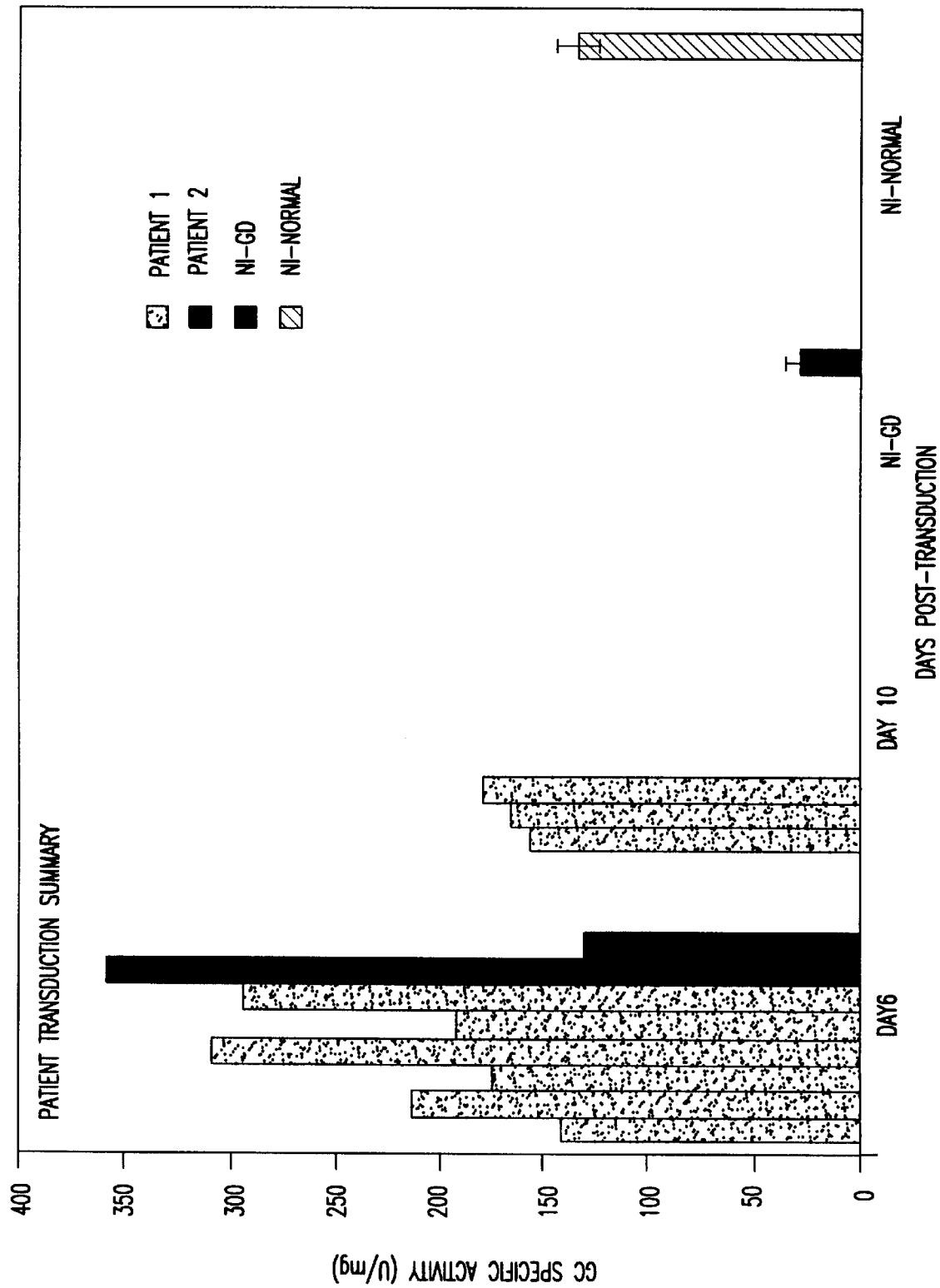
FIG. 38 Correction of GC deficiency in mobilized cells obtained from a single patient with Gaucher disease. GC activity is shown as a function of days post-transduction. NI=noninfected. GD=Gaucher disease.

FIG. 38 shows the GC activity of R-GC transduced CD34+ cells from a single Gaucher patient in multiple studies, in which GC activity levels exceeded uninfected normal cells and uninfected Gaucher cells. The mobilized cells were infected by a single infection.

EXAMPLE 13

PRODUCTION OF THE VECTOR SUPERNATANTS AND GENETICALLY CORRECTED CELLS

Master Cell Bank

A clone from the virus-producing cell line (LM 30.2.7) has been used to generate a lot-specific Master Cell Bank (MCB) in the Human Gene Therapy Applications Laboratory at the University of Pittsburgh. These banks were preserved at a low passage number. To establish a MCB, virus producer cells were grown in the standard medium in static culture and expanded in number by serial transfer to produce sufficient quantity of viable cells to freeze down a single lot of 100 ampules containing $1 \times 10^7$ cells each.

Complete medium for retroviral vector-containing supernatant production consists of: Dulbecco's Modified Eagle's Medium (DMEM), high glucose, L-glutamine (2 mM), and 10% calf serum. Also applied to the cells at the time of splitting for expansion are: Dulbecco's Phosphate Buffered Saline (PBS; 2.7 mM KCl, 1.2 mM $KH_2PO_4$, 138 mM NaCl, 8.1 mM $Na_2HPO_4$) and Trypsin-EDTA (0.05% Trypsin, 0.53 mM EDTA in Hank's Balanced Salt Solution without Ca and Mg).

Producer Cell Culture Method

LM 30.2.7 cells were thawed from cryopreserved material, washed briefly in complete medium to remove DMSO, and plated in complete medium in sterile plastic tissue culture dishes. The dishes were incubated in Forma Steri-Cult 200 Incubators at 37° C. in an atmosphere of 5% $CO_2$ in air with 90% relative humidity. They were monitored microscopically, and over several days' time the cells expanded in number until reaching confluence. The cell monolayers were then washed briefly with PBS, detached from the plastic surface with trypsin, mixed into a uniform suspension, and distributed (replated) into new dishes. The number of new dishes provides 10 to 30 times the surface area of the starting dish(es). For production of a cell bank, the process of cell number expansion followed by trypsinization and replating is repeated until sufficient cells were generated. As is customary, 100 vials containing $10^7$ cells per vial were put up for a cell bank.

Vector Supernatant Production (Lot)

For R-GC supernatant production from LM30.2.7, the expanded cells from the working cell bank are allowed to reach confluence, and medium is then replaced on a daily basis. The medium removed is frozen and stored at −80° C. in sterile containers of sufficient size to accommodate collection at each time point. At least one aliquot from each individual collection is frozen in a smaller container for determination of viral vector titer. Collection is continued daily for a period of up to two weeks.

The test aliquots are assayed for biologic activity, and acceptable individual collections are mixed in a single sterile container to form a uniform lot. This lot is then filtered through a membrane filter (0.45 $\mu$m, sterile non-pyrogenic cartridge type) using a peristaltic pump with nontoxic, nonpyrogenic tubing, and the filtered final product is refrozen in sterile containers and stored at −80° C. until use.

Stability Testing

Stability studies were performed to assess the stability of the frozen viral supernatant.

Figure 39:
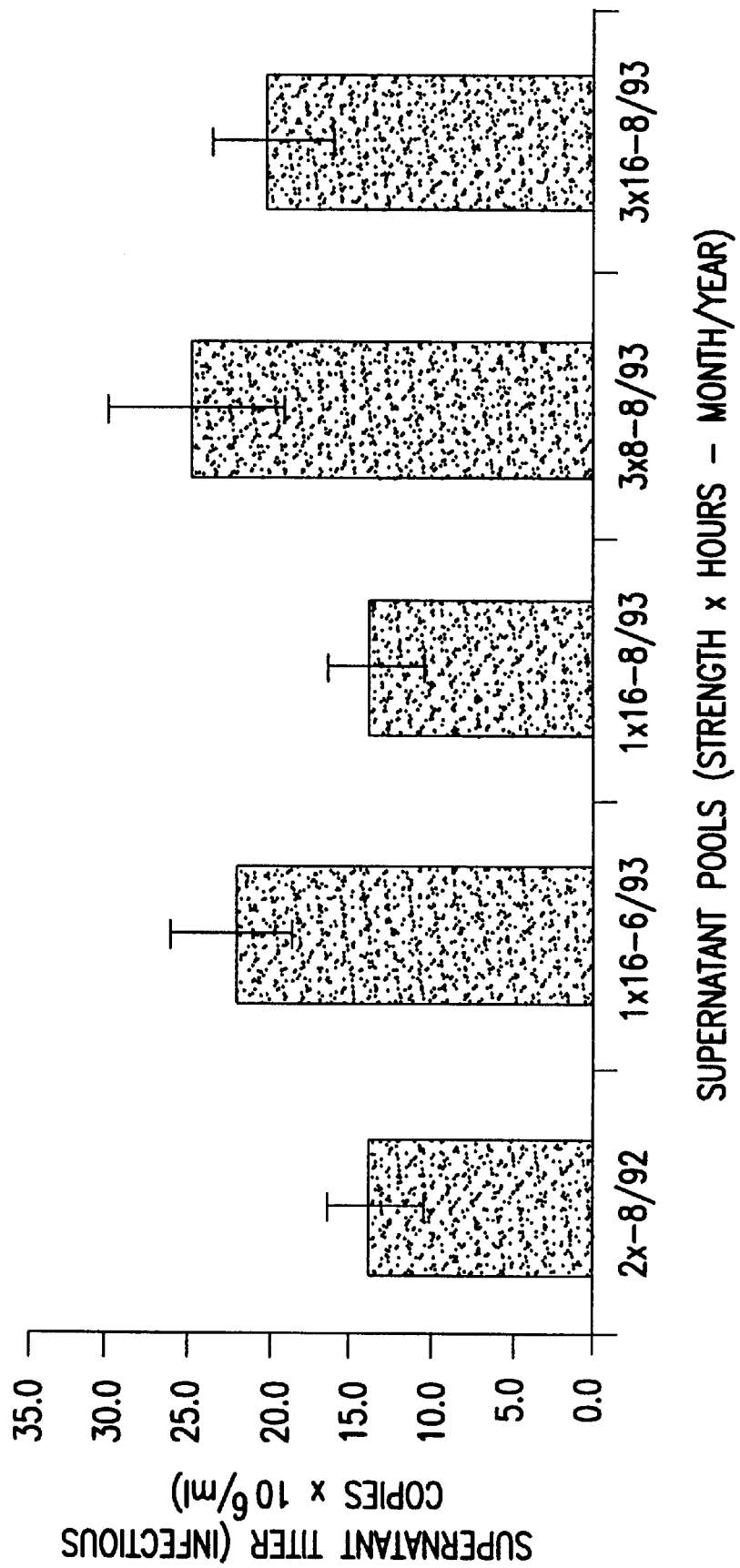
FIG. 39 Titers of cryogenically preserved vials of the YCRIP—MFG-GC producer (cc2) were determined by infection of 3T3 targets and conversion of enzyme activity to copies/ml through correlation of Southern blot hybridization intensity as described elsewhere (Bahnson, A. B., et al., *Gene Therapy* 1(3):176–184, 1994). Bars indicate the mean and standard error for n=2 to 4 supes assayed.

The stability of high titer producer, cc-2, from MFG-GC was studied over a 16 month period. The supernatant was stored at −80° C. and samples were tested every three months. Supernatant was originally collected on Aug. 14, 1992 from freshly confluent monolayers of cc-2 producers in two 15 cm dishes. Volumes of 15 ml of medium (2×) were collected following 7 hours of conditioning from each dish. This supe was filtered (0.45 um) and stored in five 15 ml tubes, 5 ml per tube, at −80° C. Tubes have been thawed and re-aliquoted into 1 ml tubes as necessary over the period of time shown. For infection, 0.5 ml of supernatant is mixed with 0.5 ml of medium and 8 $\mu$/ml of polybrene and applied to $3 \times 10^5$ target 3T3 cells on 6 cm dishes ($1.5 \times 10^5$ cells seeded one day previous). The cells are incubated at 37° C. and gently rocked every 15 minutes for 2 hours, at which time 2 ml of fresh medium is added to each dish and incubation is resumed until harvest 2 days later. The data suggest that the supernatant is stable over the test period of 12 months (FIG. 39).

To test the stability of R-GC/LM30 clones, cryogenically preserved LM30 cells were thawed and re-expanded to confluent monolayers, from which supernatants have been tested and compared with previously prepared supernatant. The titers of these supernatants were not significantly different from those obtained prior to cryogenic storage.

EXAMPLE 14

ISOLATION, ENRICHMENT AND TRANSDUCTION OF AUTOLOGOUS CD34+ CELLS

G-CSF Mobilization

G-CSF mobilization is used in patients with Gaucher Disease to increase the number of CD34+ cells in the blood. Candidates receive G-CSF at a dosage of 5 $\mu$g/kg/day by subcutaneous injection on consecutive days.

Leukopheresis

Leukopheresis procedures are continued on a daily schedule until a total mononuclear cell (MNC) yield of $7\times10^8$/kg is obtained. It is anticipated that 3–5 collections are necessary.

Seven to ten (7–10) liters of the patient blood is processed per procedure, depending on the patient's total blood volume hematocrit. Each leukopheresis product is enriched for CD34+ cells on the day of collection.

Enrichment of CD34+ Cells

Leukopheresis product is enriched for CD34+ cells using the Ceprate™ SC Stem Cell Concentrator (CellPro, Inc.). The cells are labeled with the 12.8 biotinylated anti-CD34+ antibody and loaded on to a CellPro column which permits separation of the CD34+ cells. Typical enrichment is 40–50 fold and the cells are usually more than 80% pure by FACS analysis. At the end of the separation, the CD34+ cells are viably frozen. The CD34+ cells are pooled before transduction.

Transduction of CD34+ cells

The pooled human CD34+ cells from peripheral blood are suspended in medium containing a mixture of cytokines. The mixture consists of rhSCF (10 ng/ml), rhIL-6 (10 ng/ml) and rhIL-3 (10 ng/ml) and long term bone marrow culture medium (LTBMC). LTBMC consists of Iscove's Modified Dulbecco's Medium (Gibco BRL) containing 12.5% horse serum (Hyclone Laboratories), 12.5% fetal bovine serum (Hyclone Laboratories), 1 mm mercaptoethanol, 1 mm alpha thioglycerol, 2 mM L-glutamine, and 1 mg/ml hydrocortisone. Cytokines are purchased from Preprotek, Inc. (Rocky Hill, N.J.). The cells are placed into a 10 cm dish at an approximate concentration of $2\times10^5$. The cells are pre-incubated in this mixture for 24 hours.

For infection, the viral supernatant is added to the cells, three times over 36 hours. Protamine sulfate is added to yield a final concentration of 4 mg/ml. Cell number is measured by counting suspended cells using a hemacytometer. The cells are pelleted by centrifugation at 500 g for 15 minutes. The pellet is then washed twice in cold PBS and resuspended at a cell concentration of $1\times10^7$/ml and viably frozen. The frozen cells are thawed slowly to maintain viability and prepared for administration to the patient by washing twice in PBS.

Testing of the Transduced CD34+ Cells

Transduction efficiency of the transduced CD34+ final product is monitored by PCR of CFU-GM clonogenic assays to determine the presence of the GC gene, Southern blotting to determine GC copy number, GC enzyme activity, or immunocytochemistry to detect GC protein.

For PCR analysis, a reaction mixture is made and aliquotted to each of the sample tubes, such that the final PCR reaction contains 200 $\mu$M of each dNTP, 0.5 units Taq polymerase (Amplitaq® (Perkin-Elmer)), 2 mM $MgCl_2$, and 0.4 $\mu$M of each primer in $dH_2O$. The final reaction volume is 50 $\mu$l. A pair of primers AB1 and AB2 is used, one which hybridizes to the GC cDNA region and the other to the viral sequence, respectively, to yield a unique 407 bp amplification product. (primers AB1: 5' ACG GCA TGG CAG CTT GGA TA 3' (SEQ ID NO: 1), AB2: 5' AGT AGC AAA TTT TGG GCA GG 3' (SEQ ID NO: 2)). Thermal cycling is performed on a Gene Amp PCR system 960 as follows: 94° C.×5 minutes for an initial denaturing cycle, then 30 cycles of 94° C.×45 seconds, 58° C.×45 seconds, 72° C.×30 seconds. The PCR products are resolved on a 6% acrylamide or 2% agarose gel. The bands are visualized by ethidium bromide and UV light.

Cells to be assayed for GC activity are washed twice in PBS, pelleted and stored at −80° C. prior to analysis. Pellets are thawed and extracted in cold 50 mM potassium phosphate buffer (pH 6.5) containing 2.5 mg/ml Triton X-100. Ultrasonification is used to disperse and lyse the cells, followed by 15 minute centrifugation in a microfuge at 4° C. to yield a clear supernatant for analysis Enzyme activity is determined by addition of 10 mM 4-methylumbelliferyl-β-D-glucopyranoside (Sigma Chemical Co.) in citric acid-sodium phosphate (0.12M) buffer (pH 5.4) containing 2.5 mg/ml sodium taurocholate, 2 mg/ml Triton X-100, and 10 mg/ml bovine serum albumin. The reaction is terminated after 30 minutes at 37° C. by addition of 0.17M glycine-carbonate buffer (pH 10.4), and the fluorescence of the 4-methylumbelliferone product is measured with a fluorometer. Protein concentration is determined using bicinchoninic acid according to manufacturer's instructions (Pierce Chemical Co.). The specific enzymatic activity of GC is expressed as nmoles per hour per mg of protein (U/mg).

Immunochemical detection of the human GC protein is performed according to manufacturers directions using the Vectastain ABC Kit (vector Laboratories). This kit contains a biotinylated antimouse IgG and produced an avidin biotin peroxidase complex monoclonal antibody 8E4 was used as the primary antibody. Cells are identified by staining with the horseradish peroxidase substrate 3-amino-9-ethyl-carbazole (Sigma Chemical Co.) and by counterstaining with hematoxylin. Negative controls are Gaucher patient cells. Positive controls are the CC-2 cell line. These producer cells are known transduced cells expressing the human GC protein.

EXAMPLE 15

GENE THERAPY FOR GAUCHER DISEASE

The CD34+ enriched fraction of autologous cells isolated from a Gaucher patient and transduced with R-GC to genetically correct the inability to synthesize functional GC enzymatic activity (verified as described in Example 14, supra) is transplanted back to the patient, without bone marrow ablation. A therapeutically effective number of the transduced CD34+ cells (e.g., $2\times10^6$/kg) are reintroduced into the patient by infusion, so as to provide a therapeutically effective level of GC activity.

Periodically thereafter, a sample of blood from the patient is removed and peripheral blood leukocytes (PBL) are isolated to assay for GC enzyme activity. If the GC activity is not increased at least 2-fold above the pre-treatment level, transplantation is repeated. Transplantation may be repeated up to four times in the first year.

PBL are monitored monthly to assay for the presence of the transduced GC gene, and for GC enzyme activity (as described in Example 14, supra).

Figure 40:
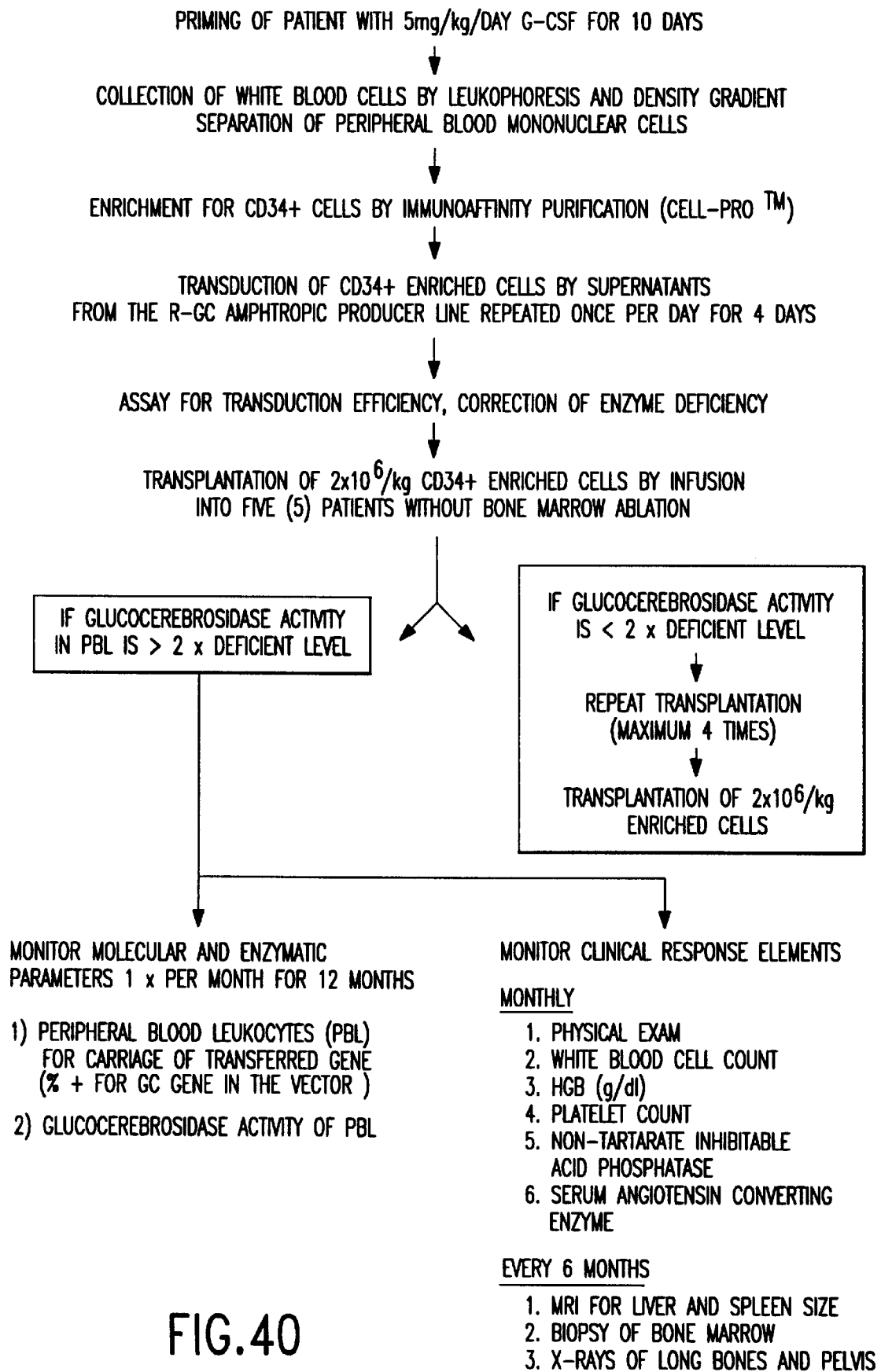
FIG. 40 Flow sheet for clinical trial of gene therapy for Gaucher disease using the retroviral vector R-GC.

Clinical responses to the gene therapy are monitored in treated Gaucher patients by routine blood profiling including hemoglobin level and platelet count, size of liver and spleen, bone marrow biopsy, and x-rays of long bones and the pelvis as outlined in FIG. 40.

Although the invention has been described in detail for the purposes of illustration, it is to be understood that such detail is solely for that purpose and that variations can be made therein by those skilled in the art without departing from the spirit and scope of the invention except as it may be limited by the claims.

7. The cells of claim 2, wherein the cells are human CD34+ cells.

8. The cells of claim 2, wherein the retroviral vector is R-GC.

9. The cells of claim 2, wherein the retroviral vector is MFG-GC.

10. The cells of claim 7, wherein the retroviral vector is R-GC.

11. The cells of claim 7, wherein the retroviral vector is MFG-GC.

12. A retroviral vector selected from the group consisting of R-GC and MFG-GC.

13. A method for providing biologically active glucocerebrosidase to the cell of an individual with Gaucher disease, comprising:

a) isolating autologous bone marrow from the individual with Gaucher disease;

---

---

We claim:

1. A human hematopoietic progenitor cell transduced with a retroviral vector, said vector comprising and expressing a DNA molecule that codes for glucocerebrosidase, wherein the transduced cell provides individual with Gaucher disease biologically active glucocerebrosidase.

2. The human hematopoietic cell of claim 1, wherein said cell is a hematopoietic stem cell.

3. The cells of claim 1, wherein the retroviral vector is R-GC.

4. The cells of claim 1, wherein the retroviral vector is MFG-GC.

5. The vector of claim 1, wherein the vector is R-GC.

6. The vector of claim 1, wherein the vector is MFG-GC, as deposited with the American Type Culture Collection and assigned accession number 75,733.

b) enriching the autologous bone marrow for hemapoietic progenitor cells to obtain an enriched hematopoietic progenitor cell population;

c) transducing the enriched progenitor cell population with a retroviral vector that contains and expresses the glucocerebrosidase gene; and d) transplanting the transduced autologous progenitor cell population into the individual with Gaucher disease so as to provide to the individual biologically active glucocerebrosidase.

14. The method of claim 13, in which the hematopoietic progenitor cells are human CD34+ cells.

15. The method of claim 13, in which the retroviral vector is R-GC.

16. The method of claim 13, in which the retroviral vector is MFG-GC.

17. The method of claim 14, in which the retroviral vector is R-GC.

18. The method of claim 14, in which the retroviral vector is MFG-GC.

19. A method for providing biologically active glucocerebrosidase to the cells of an individual with Gaucher disease, comprising:

introducing an enriched bone marrow hematopoietic progenitor cell population into a Gaucher individual, said progenitor cell population having been treated in vitro to insert therein a DNA molecule encoding human glucocerebrosidase protein, said hematopoietic progenitor cell population expressing in said Gaucher individual biologically active glucocerebrosidase protein.

20. The method of claim 19, in which the enriched bone marrow hemapoietic progenitor cell population comprises human CD34+ cells.

21. The method of claim 13, wherein the transducing step is performed by centrifuging the hematopoietic progenitor cells with a retroviral containing supernatant.

22. The method of claim 19, wherein the DNA molecule encoding human glucocerebrosidase is inserted into the hematopoietic progenitor cell population by centrifuging the hematopoietic progenitor cells with a retroviral containing supernatant so as to effect transduction of the cell population.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

ACGGCATGGC AGCTTGGATA                                                   20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

AGTAGCAAAT TTTGGGCAGG                                                   20